US010006917B2

(12) United States Patent
Dai et al.

(10) Patent No.: US 10,006,917 B2
(45) Date of Patent: Jun. 26, 2018

(54) METHODS AND COMPOSITIONS RELATING TO SUPER-RESOLUTION IMAGING AND MODIFICATION

(71) Applicant: President and Fellows of Harvard College, Cambridge, MA (US)

(72) Inventors: Mingjie Dai, Boston, MA (US); Peng Yin, Brookline, MA (US)

(73) Assignee: President and Fellows of Harvard College, Cambridge, MA (US)

(*) Notice: Subject to any disclaimer, the term of this patent is extended or adjusted under 35 U.S.C. 154(b) by 423 days.

(21) Appl. No.: 14/742,662

(22) Filed: Jun. 17, 2015

(65) Prior Publication Data
US 2016/0169903 A1  Jun. 16, 2016

Related U.S. Application Data

(63) Continuation-in-part of application No. PCT/US2014/070394, filed on Dec. 15, 2014.

(51) Int. Cl.
*G01N 33/58* (2006.01)
*G01N 21/64* (2006.01)
*C40B 80/00* (2006.01)

(52) U.S. Cl.
CPC .......... *G01N 33/582* (2013.01); *G01N 21/64* (2013.01); *G01N 2223/401* (2013.01); *G01N 2223/42* (2013.01); *G01N 2458/10* (2013.01)

(58) Field of Classification Search
CPC .............. G01N 33/582; G01N 21/64; G01N 2223/401; G01N 2223/42; G01N 2458/10
See application file for complete search history.

(56) References Cited

U.S. PATENT DOCUMENTS

| | | | |
|---|---|---|---|
| 8,481,714 B2 | 7/2013 | Fujimoto et al. | |
| 8,599,388 B1 | 12/2013 | Van Dijk et al. | |
| 8,658,780 B2 | 2/2014 | Pierce et al. | |
| 9,234,846 B2 | 1/2016 | Kalkbrenner et al. | |
| 2002/0150943 A1 | 10/2002 | Stanton et al. | |
| 2008/0032414 A1 | 2/2008 | Zhuang et al. | |
| 2013/0261019 A1 | 10/2013 | Lin et al. | |
| 2016/0033411 A1 | 2/2016 | Barish et al. | |
| 2016/0312272 A1 | 10/2016 | Barish et al. | |

FOREIGN PATENT DOCUMENTS

WO   WO 2013/090360 A2   6/2013

OTHER PUBLICATIONS

[No Author Listed] DLP® 0.95 1080p 2 x LVDS Type A DMD. Retrieved (Mar. 13, 2015) from: <www.ti.com/lit/ds/dlps025b/dlps025b.pdf>.

[No Author Listed] DNA origami scaffolds for cryo-EM visualization of membrane associated complexes. University of Michigan. Project ID: 377. Last accessed from http://mcubed.umich.edu/projects/dna-origami-scaffolds-cryo-em-visualization-membrane-associated-complexes on Nov. 12, 2015.

(Continued)

*Primary Examiner* — Jeremy C Flinders
(74) *Attorney, Agent, or Firm* — Wolf, Greenfield & Sacks, P.C.

(57) ABSTRACT

This disclosure provides methods for generating super-resolution patterns of molecules on substrates.

21 Claims, 14 Drawing Sheets

(56) References Cited

OTHER PUBLICATIONS

[No Author Listed] Scientists watch a chemical bond break using molecule's electrons. University of Ottawa. ScienceDaily. www.sciencedaily.com/releases/2010/07/100728131709.htm (accessed Mar. 19, 2015).

Agasti et al., Dual imaging and photoactivated nanoprobe for controlled cell tracking. Small. Jan. 28, 2013;9(2):222-7. doi: 10.1002/smll.201201007. Epub Sep. 21, 2012.

Agasti et al., Photoregulated release of caged anticancer drugs from gold nanoparticles. J Am Chem Soc. Apr. 29, 2009;131(16):5728-9. doi: 10.1021/ja900591t.

Amouyal et al., On the Photoionization Energy Threshold of Tryptophan in Aqueous Solutions. Photochem Photobiol. 1979;29(6):1071-7.

Anshelevich et al., Slow relaxational processes in the melting of linear biopolymers: a theory and its application to nucleic acids. Biopolymers. Jan. 1984;23(1):39-58.

Backlund et al., Simultaneous, accurate measurement of the 3D position and orientation of single molecules. Proc Natl Acad Sci U S A. Nov. 20, 2012;109(47):19087-92. doi:10.1073/pnas.1216687109. Epub Nov. 5, 2012.

Badieirostami et al., Three-dimensional localization precision of the double-helix point spread function versus astigmatism and biplane. Appl Phys Lett. Oct. 18, 2010;97(16):161103.

Bai et al., Cryo-EM structure of a 3D DNA-origami object. Proc Natl Acad Sci U S A. Dec. 4, 2012;109(49):20012-7. doi:10.1073/pnas.1215713109. Epub Nov. 19, 2012.

Bates et al., Multicolor super-resolution imaging with photo-switchable fluorescent probes. Science. Sep. 21, 2007;317(5845):1749-53. Epub Aug. 16, 2007.

Bates et al., Short-range spectroscopic ruler based on a single-molecule optical switch. Phys Rev Lett. Mar. 18, 2005;94(10):108101. Epub Mar. 15, 2005.

Belyy et al., Processive cytoskeletal motors studied with single-molecule fluorescence techniques. FEBS Lett. Oct. 1, 2014;588(19):3520-5. doi:10.1016/j.febslet.2014.05.040. Epub May 29, 2014.

Ben-Shem et al., The structure of the eukaryotic ribosome at 3.0 Å resolution. Science. Dec. 16, 2011;334(6062):1524-9. doi: 10.1126/science.1212642. Epub Nov. 17, 2011.

Bernard et al., Acquired dendritic channelopathy in temporal lobe epilepsy. Science. Jul. 23, 2004;305(5683):532-5.

Bernstein et al., Optogenetic tools for analyzing the neural circuits of behavior. Trends Cogn Sci. Dec. 2011;15(12):592-600. doi:10.1016/j.tics.2011.10.003. Epub Nov. 4, 2011.

Betzig et al., Imaging intracellular fluorescent proteins at nanometer resolution. Science. Sep. 15, 2006;313(5793):1642-5. Epub Aug. 10, 2006.

Bisby et al., Nanoscale hydroxyl radical generation from multiphoton ionization of tryptophan. Photochem Photobiol. Jan.-Feb. 2009;85(1):353-7. doi:10.1111/j.1751-1097.2008.00447.x.

Borisenko et al., Simultaneous optical and electrical recording of single gramicidin channels. Biophys J. Jan. 2003;84(1):612-22.

Brohawn et al., Mechanosensitivity is mediated directly by the lipid membrane in TRAAK and TREK1 K+ channels. Proc Natl Acad Sci U S A. Mar. 4, 2014;111(9):3614-9. doi:10.1073/pnas.1320768111. Epub Feb. 18, 2014.

Bullock, Messengers, motors and mysteries: sorting of eukaryotic mRNAs by cytoskeletal transport. Biochem Soc Trans. Oct. 2011;39(5):1161-5. doi:10.1042/BST0391161.

Cadilhe et al., Random sequential adsorption: from continuum to lattice and pre-patterned substrates. J Phys Condens Matt. 2007;19:065124.

Cao et al., Presynaptic Ca2+ channels compete for channel type-preferring slots in altered neurotransmission arising from Ca2+ channelopathy. Neuron. Aug. 5, 2004;43(3):387-400.

Chapman et al., Femtosecond X-ray protein nanocrystallography. Nature. Feb. 3, 2011;470(7332):73-7. doi: 10.1038/nature09750.

Chen et al., A Quantitative Theory Model of a Photobleaching Mechanism. Chinese Phys Lett. 1940;20(11):1940-3.

Chen et al., High-order photobleaching of green fluorescent protein inside live cells in two-photon excitation microscopy. Biochem Biophys Res Commun. Mar. 15, 2002;291(5):1272-5.

Cheng et al., A primer to single-particle cryo-electron microscopy. Cell. Apr. 23, 2015;161(3):438-49. doi:10.1016/j.cell.2015.03.050.

Conley et al., Cy3-Cy5 covalent heterodimers for single-molecule photoswitching. J Phys Chem B. Sep. 25, 2008;112(38):11878-80. doi:10.1021/jp806698p. Epub Aug. 28, 2008.

De La Cruz et al., Navigating the cell: how motors function in vivo. J Cell Sci. Jul. 15, 2014;127(Pt 14):2997-8. doi: 10.1242/jcs.156414.

Dempsey et al., Evaluation of fluorophores for optimal performance in localization-based super-resolution imaging. Nat Methods. Nov. 6, 2011;8(12):1027-36. doi: 10.1038/nmeth.1768.

Dempsey et al., Photoswitching mechanism of cyanine dyes. J Am Chem Soc. Dec. 30, 2009;131(51):18192-3. doi:10.1021/ja904588g.

Dittrich et al., Photobleaching and stabilization of. fluorophores used for single-molecule analysis. with one- and two-photon excitation. Applied Physics B. 2001;73(8):829-37.

Donnert et al., Macromolecular-scale resolution in biological fluorescence microscopy. Proc Natl Acad Sci U S A. Aug. 1, 2006;103(31):11440-5. Epub Jul. 24, 2006.

Donnert et al., Major signal increase in fluorescence microscopy through dark-state relaxation. Nat Methods. Jan. 2007;4(1):81-6. Epub Dec. 10, 2007.

Dorval et al., Channel noise is essential for perithreshold oscillations in entorhinal stellate neurons. J Neurosci. Oct. 26, 2005;25(43):10025-8.

Douglas et al., DNA-nanotube-induced alignment of membrane proteins for NMR structure determination. Proc Natl Acad Sci U S A. Apr. 17, 2007;104(16):6644-8. Epub Apr. 2, 2007.

Eggeling et al., Molecular photobleaching kinetics of Rhodamine 6G by one- and two-photon induced confocal fluorescence microscopy. Chemphyschem. May 2005;6(5):791-804.

Ellis-Davies, Caged compounds: photorelease technology for control of cellular chemistry and physiology. Nat Methods. Aug. 2007;4(8):619-28.

Epifanovsky et al., The effect of oxidation on the electronic structure of the green fluorescent protein chromophore. J Chem Phys. Mar. 21, 2010;132(11):115104. doi: 10.1063/1.3336425.

Feng et al., Cinnamate-based DNA photolithography. Nat Mater. Aug. 2013;12(8):747-53. doi:10.1038/nmat3645. Epub May 19, 2013.

Fontoura et al., A conserved biogenesis pathway for nucleoporins: proteolytic processing of a 186-kilodalton precursor generates Nup98 and the novel nucleoporin, Nup96. J Cell Biol. Mar. 22, 1999;144(6):1097-112.

Fujimo et al., Quick, Selective and Reversible Photocrosslinking Reaction between 5-Methylcytosine and 3-Cyanovinylcarbazole in DNA Double Strand. Int J Mol Sci. Mar. 12, 2013;14(3):5765-74. doi:10.3390/ijms14035765.

Fujimoto et al., Site-specific photochemical RNA editing. Chem Commun (Camb). Oct. 28, 2010;46(40):7545-7. doi:10.1039/c0cc03151h. Epub Sep. 17, 2010.

González et a., Cell-based assays and instrumentation for screening ion-channel targets. Drug Discov Today. Sep. 1999;4(9):431-439.

Görner, Direct and sensitized photoprocesses of bis-benzimidazole dyes and the effects of surfactants and DNA. Photochem Photobiol. Apr. 2001;73(4):339-48.

Grotjohann et al., Diffraction-unlimited all-optical imaging and writing with a photochromic GFP. Nature. Sep. 11, 2011;478(7368):204-8. doi:10.1038/nature10497.

Heilemann et al., Carbocyanine dyes as efficient reversible single-molecule optical switch. J Am Chem Soc. Mar. 23, 2005;127(11):3801-6.

Heisterkamp et al., Fs-laser scissors for photobleaching, ablation in fixed samples and living cells, and studies of cell mechanics. Methods Cell Biol. 2007;82:293-307.

(56) References Cited

OTHER PUBLICATIONS

Hell et al., Breaking the diffraction resolution limit by stimulated emission: stimulated-emission-depletion fluorescence microscopy. Opt Lett. Jun. 1, 1994;19(11):780-2.

Hell, Far-field optical manoscopy. Science. May 25, 2007;316(5828):1153-8.

Hell, Microscopy and its focal switch. Nat Methods. Jan. 2009;6(1):24-32. doi:10.1038/nmeth.1291.

Henry et al., Real-time measurements of DNA hybridization on microparticles with fluorescence resonance energy transfer. Anal Biochem. Dec. 15, 1999;276(2):204-14.

Hinrichsen et al., The Geometry of Random Sequential Adsorption. J. Stat. Phys. 1986;44(516):793-827.

Hirokawa et al., Kinesin superfamily motor proteins and intracellular transport. Nat Rev Mol Cell Biol. Oct. 2009;10(10):682-96. doi:10.1038/nrm2774.

Holt et al., Subcellular mRNA localization in animal cells and why it matters. Science. Nov. 27, 2009;326(5957):1212-6. doi: 10.1126/science.1176488.

Huang et al., Breaking the diffraction barrier: super-resolution imaging of cells. Cell. Dec. 23, 2010;143(7):1047-58. doi:10.1016/j.cell.2010.12.002.

Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.

Hung et al., Proteomic mapping of the human mitochondrial intermembrane space in live cells via ratiometric APEX tagging. Mol Cell. Jul. 17, 2014;55(2):332-41. doi:10.1016/j.molcel.2014.06.003. Epub Jul. 4, 2014.

Ianoul et al., Near-field scanning fluorescence microscopy study of ion channel clusters in cardiac myocyte membranes. Biophys J. Nov. 2004;87(5):3525-35. Epub Aug. 31, 2004.

Iinuma et al., Polyhedra self-assembled from DNA tripods and characterized with 3D DNA-PAINT. Science. Apr. 4, 2014;344(6179):65-9. doi:10.1126/science.1250944. Epub Mar. 13, 2014.

Ishii et al., Single molecule nanomanipulation of biomolecules. Trends Biotechnol. Jun. 2001;19(6):211-6.

Jenner et al., Crystal structure of the 80S yeast ribosome. Curr Opin Struct Biol. Dec. 2012;22(6):759-67. doi:10.1016/j.sbi.2012.07.013. Epub Aug. 8, 2012. Review.

Jones et al., Fast, three-dimensional super-resolution imaging of live cells. Nat Methods. Jun. 2011;8(6):499-508. doi:10.1038/nmeth.1605. Epub May 8, 2011.

Jones et al., Nanomaterials. Programmable materials and the nature of the DNA bond. Science. Feb. 20, 2015;347(6224):1260901. doi:10.1126/science.1260901.

Juette et al., Three-dimensional sub-100 nm resolution fluorescence microscopy of thick samples. Nat Methods. Jun. 2008;5(6):527-9. doi: 10.1038/nmeth.1211. Epub May 11, 2008.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Kalies et al., Mechanisms of high-order photobleaching and its relationship to intracellular ablation. Biomed Opt Express. Mar. 4, 2011;2(4):805-16. doi:10.1364/Boe.2.000816.

Kao et al., Tracking of single fluorescent particles in three dimensions: use of cylindrical optics to encode particle position. Biophys J. Sep. 1994;67(3):1291-300.

Kato et al., High-resolution structural analysis of a DNA nanostructure by cryoEM. Nano Lett. Jul. 2009;9(7):2747-50. doi: 10.1021/n1901265n.

Ke et al., DNA brick crystals with prescribed depths. Nat Chem. Nov. 2014;6(11):994-1002. doi: 10.1038/nchem.2083. Epub Oct. 19, 2014.

Kole et al., Action potential generation requires a high sodium channel density in the axon initial segment. Nat Neurosci. Feb. 2008;11(2):178-86. doi: 10.1038/nn2040. Epub Jan. 20, 2008.

Kuetemeyer et al., Influence of laser parameters and staining on femtosecond laser-based intracellular nanosurgery. Biomed Opt Express. Aug. 10, 2010;1(2):587-597.

Lee et al., The double-helix microscope super-resolves extended biological structures by localizing single blinking molecules in three dimensions with nanoscale precision. Appl Phys Lett. Apr. 9, 2012;100(15):153701-1537013.

Lehr et al., Real-time detection of nucleic acid interactions by total internal reflection fluorescence. Anal Chem. May 15, 2003;75(10):2414-20.

Levskaya et al., Spatiotemporal control of cell signalling using a light-switchable protein interaction. Nature. Oct. 15, 2009;461(7266):997-1001. doi: 10.1038/nature08446. Epub Sep. 13, 2009.

Lin et al., Submicrometre geometrically encoded fluorescent barcodes self-assembled from DNA. Nat Chem. Oct. 2012;4(10):832-9.

Lusic et al., Improved synthesis of the two-photon caging group 3-nitro-2-ethyldibenzofuran and its application to a caged thymidine phosphoramidite. Org Lett. Mar. 5, 2010;12(5):916-9. doi:10.1021/01902807q.

Manfrinato et al., Determining the resolution limits of electron-beam lithography: direct measurement of the point-spread function. Nano Lett. Aug. 13, 2014;14(8):4406-12. doi:10.1021/n15013773. Epub Jun. 30, 2014.

Manning, The molecular theory of polyelectrolyte solutions with applications to the electrostatic properties of polynucleotides. Q Rev Biophys. May 1978;11(2):179-246.

Martell et al., Engineered ascorbate peroxidase as a genetically encoded reporter for electron microscopy. Nat Biotechnol. Nov. 2012;30(11):1143-8. doi:10.1038/nbt.2375. Epub Oct. 21, 2012.

Martin, Functional Synthetic Dna Nanostructures. Dissertation. Technische Universität München, Laboratory for Biomolecular Nanotechnology. Filed on Mar. 12, 2013.

Michel et al., Optical study of DNA surface hybridization reveals DNA surface density as a key parameter for microarray hybridization kinetics. Biophys J. Feb. 1, 2007;92(3):999-1004. Epub Nov. 3, 2006.

Nannenga et al., High-resolution structure determination by continuous-rotation data collection in MicroED. Nat Methods. Sep. 2014;11(9):927-30. doi: 10.1038/nmeth.3043. Epub Aug. 3, 2014.

Nannenga et al., Protein structure determination by MicroED. Curr Opin Struct Biol. Aug. 2014;27:24-31. doi: 10.1016/j.sbi.2014.03.004. Epub Apr. 5, 2014.

Nikogosyan et al., Two-photon ionization and dissociation of liquid water by powerful laser UV radiation. Chem Phys. 1983;77(1):131-43.

Olejnik et al., Photocleavable biotin derivatives: a versatile approach for the isolation of biomolecules. Proc Natl Acad Sci U S A. Aug. 1, 1995;92(16):7590-4.

Ormö et al., Crystal structure of the Aequorea victoria green fluorescent protein. Science. Sep. 6, 1996;273(5280):1392-5.

Patterson et al., Photobleaching in two-photon excitation microscopy. Biophys J. Apr. 2000;78(4):2159-62.

Pavani et al., Three dimensional tracking of fluorescent microparticles using a photon-limited double-helix response system. Opt Express. Dec. 22, 2008;16(26):22048-57.

Pavani et al., Three-dimensional, single-molecule fluorescence imaging beyond the diffraction limit by using a double-helix point spread function. Proc Natl Acad Sci U S A. Mar. 3, 2009;106(9):2995-9. doi: 10.1073/pnas.0900245106. Epub Feb. 11, 2009.

Pertsinidis et al., Subnanometre single-molecule localization, registration and distance measurements. Nature. Jul. 29, 2010;466(7306):647-51. doi:10.1038/nature09163. Epub Jul. 7, 2010.

Petruska et al., Enthalpy-entropy compensation in DNA melting thermodynamics. J Biol Chem. Jan. 13, 1995;270(2):746-50.

Piestun et al., Propagation-invariant wave fields with finite energy. J Opt Soc Am A Opt Image Sci Vis. Feb. 2000;17(2):294-303.

Pinheiro et al., Challenges and opportunities for structural DNA nanotechnology. Nat Nanotechnol. Nov. 6, 2011;6(12):763-72. doi:10.1038/nnano.2011.187.

(56) References Cited

OTHER PUBLICATIONS

Ram et al., A novel approach to determining the three-dimensional location of microscopic objects with applications to 3D particle tracking. Proc SPIE. Feb. 14, 2007;6443:7 pages.
Rasnik et al., Nonblinking and long-lasting single-molecule fluorescence imaging. Nat Methods. Nov. 2006;3(11):891-3. Epub Oct. 1, 2006.
Record et al., Thermodynamic analysis of ion effects on the binding and conformational equilibria of proteins and nucleic acids: the roles of ion association or release, screening, and ion effects on water activity. Q Rev Biophys. May 1978;11(2):103-78.
Redmond et al., Excited State Relaxation in Cyanine Dyes: A Remarkably Efficient Reverse Intersystem Crossing from Upper Triplet Levels. J Phys Chem. 1997;101(15):2773-7.
Reindl et al., Higher excited-state triplet-singlet intersystem crossing of some organic dyes. Chem Phys. Nov. 1, 1996;211(1-3):431-9.
Reuther et al., Primary Photochemical Processes in Thymine in Concentrated Aqueous Solution Studied by Femtosecond UV Spectroscopy. J Chem Phys. 1996;100(13):5570-7.
Rhee et al., Proteomic mapping of mitochondria in living cells via spatially restricted enzymatic tagging. Science. Mar. 15, 2013;339(6125):1328-31. doi: 10.1126/science.1230593. Epub Jan. 31, 2013.
Ringemann et al., Enhancing fluorescence brightness: effect of reverse intersystem crossing studied by fluorescence fluctuation spectroscopy. Chemphyschem. Mar. 14, 2008;9(4):612-24. doi:10.1002/cphc.200700596.
Rust et al., Sub-diffraction-limit imaging by stochastic optical reconstruction microscopy (STORM). Nat Methods. Oct. 2006;3(10):793-5. Epub Aug. 9, 2006.
Ruuckmann et al., On the Influence of Higher Excited States on the ISC Quantum Yield of Octa-aL-alkyloxy-substituted Zn-Phthalocyanine Molecules Studied by Nonlinear Absorption. Photochem Photobiol. Nov. 1997;66(5):576-84.
Sabanayagam et al., Long time scale blinking kinetics of cyanine fluorophores conjugated to DNA and its effect on Förster resonance energy transfer. J Chem Phys. Dec. 8, 2005;123(22):224708.
Santalucia, A unified view of polymer, dumbbell, and oligonucleotide DNA nearest-neighbor thermodynamics. Proc Natl Acad Sci U S A. Feb. 17, 1998;95(4):1460-5.
Sasmal et al., Single-molecule patch-clamp FRET microscopy studies of NMDA receptor ion channel dynamics in living cells: revealing the multiple conformational states associated with a channel at its electrical off state. J Am Chem Soc. Sep. 17, 2014;136(37):12998-3005. doi:10.1021/ja506231j. Epub Sep. 5, 2014.
Schmidt et al., A fully genetically encoded protein architecture for optical control of peptide ligand concentration. Nat Commun. 2014;5:3019. doi:10.1038/ncomms4019.
Schneidman et al., Ion channel stochasticity may be critical in determining the reliability and precision of spike timing. Neural Comput. Oct. 1, 1998;10(7):1679-703.
Sharonov et al., Wide-field subdiffraction imaging by accumulated binding of diffusing probes. Proc Natl Acad Sci U S A. Dec. 12, 2006;103(50):18911-6. Epub Dec. 1. 2006.
Shi et al., Three-dimensional electron crystallography of protein microcrystals. Elife. Nov. 19, 2013;2:e01345. doi:10.7554/eLife.01345.
Shi, A glimpse of structural biology through X-ray crystallography. Cell. Nov. 20, 2014;159(5):995-1014. doi: 10.1016/j.cell.2014.10.051.
Shigeno et al., Quick regulation of mRNA functions by a few seconds of photoirradiation. Org Biomol Chem. Oct. 14, 2012;10(38):7820-5. doi: 10.1039/c2ob25883h.
Shuai et al., Optimal ion channel clustering for intracellular calcium signaling. Proc Natl Acad Sci U S A. Jan. 21, 2003;100(2):506-10. Epub Jan. 7, 2003.
Smith et al., Fast, single-molecule localization that achieves theoretically minimum uncertainty. Nat Methods. May 2010;7(5):373-5. doi: 10.1038/nmeth.1449. Epub Apr. 4, 2010.
Song et al., Influence of the triplet excited state on the photobleaching kinetics of fluorescein in microscopy. Biophys J. Jun. 1996;70(6):2959-68.
Szilard, On the decrease of entropy in a thermodynamic system by the intervention of intelligent beings. Zeitschrift fur Physik. 1929;53:840-856. German.
Szychowski et al., Cleavable biotin probes for labeling of biomolecules via azide-alkyne cycloaddition. J Am Chem Soc. Dec. 29, 2010;132(51):18351-60. doi:10.1021/ja1083909. Epub Dec. 8, 2010.
Tadross et al., Ca2+ channel nanodomains boost local Ca2+ amplitude. Proc Natl Acad Sci U S A. Sep. 24, 2013;110(39):15794-9. doi:10.1073/pnas.1313898110. Epub Sep. 9, 2013.
Tirlapur et al., Femtosecond near-infrared laser pulses elicit generation of reactive oxygen species in mammalian cells leading to apoptosis-like death. Exp Cell Res. Feb. 1, 2001;263(1):88-97.
Tokumura et al., Reverse intersystem crossing from higher triplet to excited singlet in 2,2'-bipyridine-3,3'-diol phototautomer. J Photochem Photobiol. Aug. 2, 1994;81(3):151-8.
Tokunaga et al., Highly inclined thin illumination enables clear single-molecule imaging in cells. Nat Methods. Feb. 2008;5(2):159-61. doi: 10.1038/nmeth1171. Epub Jan. 6, 2008. Erratum in: Nat Methods. May 2008;5(5):455.
Torquato et al., Random sequential addition of hard spheres in high Euclidean dimensions. Phys Rev E Stat Nonlin Soft Matter Phys. Dec. 2006;74(6 Pt 1):061308. Epub Dec. 20, 2006.
Toyabe et al., Experimental demonstration of information-to-energy conversion and validation of the generalized Jarzynski equality. Nature Phys. 2010;6:988-92.
Uno et al., A spontaneously blinking fluorophore based on intramolecular spirocyclization for live-cell super-resolution imaging. Nat Chem. Aug. 2014;6(8):681-9. doi: 10.1038/nchem.2002. Epub Jul. 20, 2014.
Vale, The molecular motor toolbox for intracellular transport. Cell. Feb. 21, 2003;112(4):467-80.
Van De Linde et al., Direct stochastic optical reconstruction microscopy with standard fluorescent probes. Nat Protoc. Jun. 16, 2011;6(7):991-1009. doi:10.1038/nprot.2011.336.
Van Den Berg et al., Molecular motors in cargo trafficking and synapse assembly. Adv Exp Med Biol. 2012;970:173-96. doi:10.1007/978-3-7091-0932-8_8.
Vaughan et al., Phosphine quenching of cyanine dyes as a versatile tool for fluorescence microscopy. J Am Chem Soc. Jan. 30, 2013;135(4):1197-200. doi: 10.1021/ja3105279. Epub Jan. 17, 2013.
Vaughan et al., Ultrabright photoactivatable fluorophores created by reductive caging. Nat Methods. Dec. 2012;9(12):1181-4. doi: 10.1038/nmeth.2214. Epub Oct. 28, 2012.
Vieregg et al., Selective nucleic acid capture with shielded covalent probes. J Am Chem Soc. Jul. 3, 2013;135(26):9691-9. doi:10.1021/ja4009216. Epub Jun. 18, 2013.
Von Middendorff et al., Isotropic 3D Nanoscopy based on single emitter switching. Opt Express. Dec. 8, 2008;16(25):20774-88.
White et al., Noise from voltage-gated ion channels may influence neuronal dynamics in the entorhinal cortex. J Neurophysiol. Jul. 1998;80(1):262-9.
Widengren et al., Strategies to improve photostabilities in ultrasensitive fluorescence spectroscopy. J Phys Chem A. Jan. 25, 2007;111(3):429-40.
Winfree et al., Design and self-assembly of two-dimensional DNA crystals. Nature. Aug. 6, 1998;394(6693):539-44.
Wlodawer et al., Protein crystallography for aspiring crystallographers or how to avoid pitfalls and traps in macromolecular structure determination. FEBS J. Nov. 2013;280(22):5705-36. doi:10.1111/febs.12495. Epub Sep. 18, 2013.
Wörner et al., Following a chemical reaction using high-harmonic interferometry. Nature. Jul. 29, 2010;466(7306):604-7. doi: 10.1038/nature09185.
Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.

(56) References Cited

OTHER PUBLICATIONS

Yoshimura et al., Ultrafast reversible photo-cross-linking reaction: toward in situ DNA manipulation. Org Lett. Aug. 7, 2008;10(15):3227-30. doi:10.1021/ol801112j. Epub Jun. 27, 2008.
Zadeh et al., NUPACK: Analysis and design of nucleic acid systems. J Comput Chem. Jan. 15, 2011;32(1):170-3. doi:10.1002/jcc.21596.
Zhang et al., Structural DNA nanotechnology: state of the art and future perspective. J Am Chem Soc. Aug. 13, 2014;136(32):11198-211. doi:10.1021/ja505101a. Epub Jul. 28, 2014.
Zheng et al., From molecular to macroscopic via the rational design of a self-assembled 3D DNA crystal. Nature. Sep. 3, 2009;461(7260):74-7. doi:10.1038/nature08274.
Zhong et al., Femtosecond Real-Time Probing of Reactions. 23. Studies of Temporal, Velocity, Angular, and State Dynamics from Transition States to Final Products by Femtosecond-Resolved Mass Spectrometry. J Phys Chem. 1998;102(23):4031-58.
Jungmann et al., Single-molecule kinetics and super-resolution microscopy by fluorescence imaging of transient binding on DNA origami. Nano Lett. Nov. 10, 2010;10(11):4756-61. doi: 10.1021/nl103427w.
Jungmann et al., Nanoscale imaging in DNA nanotechnology. Wiley Interdiscip Rev Nanomed Nanobiotechnol. Jan.-Feb. 2012;4(1):66-81. doi: 10.1002/wnan.173. Epub Nov. 23, 2011.
Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014. Supplementary Text and Figures; 38 pages.
Lubeck et al., Single-cell systems biology by super-resolution imaging and combinatorial labeling. Nature Methods. Jul. 2012;9(7):743-8.
Manning et al., Fabrication of patterned surfaces by photolithographic exposure of DNA hairpins carrying a novel photolabile group. J Exp Nanoscience. Feb. 1, 2010;5(1): 26-39.
Manning et al., Use of oligonucleotides carrying photolabile groups for the control of the deposition of nanoparticles in surfaces and nanoparticle association. Int J Mol Sci. 2011;12(10):7238-49. doi: 10.3390/ijms12107238. Epub Oct. 24, 2011.
Wang et al., Caged molecular beacons: controlling nucleic acid hybridization with light. Chem Commun. 2011;47:5708-10.
U.S. Appl. No. 14/811,638, filed Jul. 28, 2015, Published, 2016-00335411.
U.S. Appl. No. 15/104,570, filed Jun. 15, 2016, Pending.
PCT/US2014/070394, Apr. 3, 2015, International Search Report and Written Opinion.
PCT/US2014/070394, Jun. 30, 2016, International Preliminary Report on Patentability.
U.S. Appl. No. 15/104,570, filed Jun. 15, 2016, Published, 2016-0312272.
EP 14869597.6, May 9, 2017, Extended European Search Report.

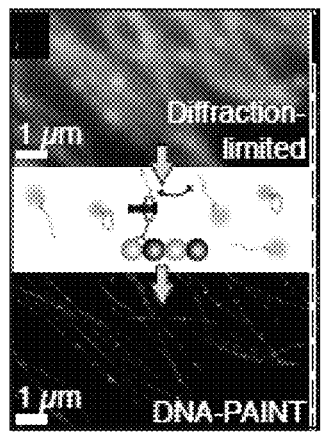 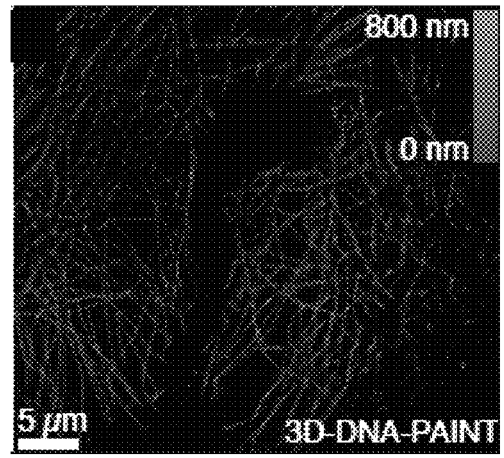
FIG. 9A　　　　　　　　　　FIG. 9B
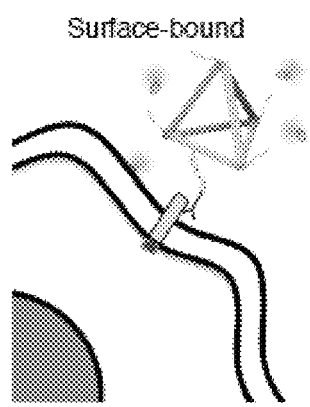 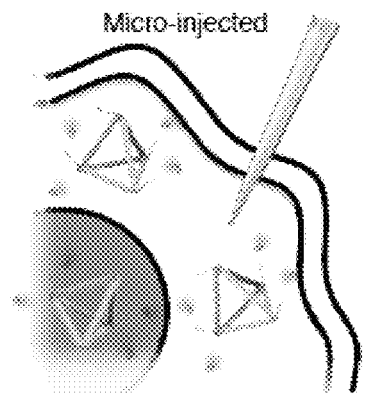
FIG. 9C　　　　　　　　　　FIG. 9D

SEQUENCE LISTING

```
<160> NUMBER OF SEQ ID NOS: 1

<210> SEQ ID NO 1
<211> LENGTH: 74
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with covalently conjugated ATTO655 dye
<220> FEATURE:
<221> NAME/KEY: misc_feature
<222> LOCATION: (15)..(16)
<223> OTHER INFORMATION: Position of photocleavable spacer

<400> SEQUENCE: 1
tagatgtatg gtctgccgga ctttttttc aatgtatttt ttttgtccgg cagaccatac     60
atctatcttc atta                                                      74
```

METHODS AND COMPOSITIONS RELATING TO SUPER-RESOLUTION IMAGING AND MODIFICATION

RELATED APPLICATIONS

This application is a continuation-in-part of and claims priority to International Application No. PCT/US2014/070394 filed Dec. 15, 2014, the entire contents of which are incorporated by reference herein.

BACKGROUND

The hallmark of modern molecular biology is the ability to manipulate and observe biological systems on the molecular scale. The precision of the manipulation and observation often determines the clarity, quality, and confidence of the knowledge that can be obtained. Super-resolution imaging methods that break the diffraction limit of light have allowed researchers to "see the previously invisible" and obtain insights at a much deeper level.

SUMMARY

The invention provides methods that allow optical manipulation of molecules with nanometer precision. Heretofore, it has been challenging to label (and to further manipulate and thereby study) a target such as a target protein in a small prescribed region of interest (such as a 5 nm-by-5 nm region of interest), while not also indiscriminately labeling another target a short distance (e.g., 10 nm) away. Provided herein are methods for super-resolution labeling that involve super-resolved optical labeling and perturbation of molecular targets with nanometer precision. These methods allow researchers to "grab the previously untouchable". This capability has a broad range of applications including but not limited to nanoscale single-cell spatial proteomics for the capture and identification of protein targets at arbitrary user-specified molecular locations in the cell, and nanoscale optogenetics for the activation/de-activation of specific ion channels at user-specified locations on the living neuron with nanometer precision.

This disclosure provides methods and compositions for patterning substrates in two or three dimensions with molecules or functionalities of interest. The methods provided herein employ probes having chemistry that allows for transient binding interactions with targets (e.g., surface conjugated nucleic acids that participate in sequence-specific binding interactions with the probes), and photocrosslinkers and/or photocleavable linkers. The methods further comprise detection of a binding event, followed by irradiation of a substrate under certain conditions (e.g., when only a single desired binding event is occurring). This process is referred to herein as a feedback process (or system) because it is the occurrence of the binding event itself which dictates and controls the timing of the irradiation event.

Thus, one aspect of this disclosure provides a method for locating and optionally obtaining partial sequence information for a target protein, comprising (1) labeling a target protein in a fixed cell or tissue with a binding partner conjugated to a docking strand, (2) repeatedly contacting the fixed cell or tissue with fluorescently-labeled imager strands that transiently bind to the docking strand, and imaging the fixed cell or tissue, thereby locating the position of the target protein within the fixed cell or tissue, optionally washing away the fluorescently-labeled imager strands, (3) contacting the fixed cell or tissue with nucleic acid probes that specifically and transiently bind to docking strands, wherein the probes comprise a photocrosslinker or a photocleavable linker, and a fluorophore, and a conjugation handle, (4) detecting binding of the probe to a target protein, (5) irradiating the fixed cell or tissue to immobilize the probe to the target protein only when a target protein present in a region of interest (or select region or user defined location or region) is bound to a probe, and (6) lysing the fixed cell or tissue and capturing the target protein onto a substrate using a nucleic acid complementary to the conjugation handle.

Various embodiments apply equally to the aspects provided herein but will for the sake of brevity be recited only once. Thus, various of the following embodiments apply equally to aspects recited below. It is also to be understood that, while methods are described in the context of a target or a protein, such methods are directed to labeling and localizing a plurality of targets or proteins. Thus, in many aspects, the methods comprise a first step of locating a plurality of targets or proteins, for example in or on a cell, followed by a second step of modifying only a subset of such targets and proteins depending on whether such targets or proteins are in a region of interest.

The fluorescently-labeled imager strands comprise a nucleotide sequence that is complementary to the docking strands. Similarly, the nucleic acid probes comprise a sequence that is complementary to a nucleotide sequence of the docking strands. Typically these complementary sequences or regions are about 8-10 nucleotides in length. In embodiments comprising a photocrosslinker, the photocrosslinker may be present in the complementary nucleotide sequence.

In some embodiments, the binding partner may be an antibody, an antibody fragment, or a nanobody.

In some embodiments, the photocrosslinker is 3-cyanovinylcarbazole. In some embodiments, the probe comprises a $^{CNV}K$ crosslinker, and optionally the docking strand comprises a T or C nucleotide in the −1 position.

In some embodiments, the photocleavable linker comprises 1-(2-nitrophenyl)ethyl. In some embodiments, the photocleavable linker comprises o-nitrobenzyl or a derivative thereof.

In some embodiments, the fluorophore emits at least $10^4$-$10^6$ photons. In some embodiments, the fluorophore is selected from the group consisting of ATTO655, Cy3b, Cy3, Cy5, Cy5.5, Alexa647 and Atto647N. In some embodiments, the fluorophore is ATTO655 or Cy3b.

In some embodiments, the fixed cell or tissue is irradiated with 366 nm to 405 nm light for less than 5 seconds, less than 1 second, or less than 0.5 seconds.

In some embodiments, the nucleic acid probes comprise a nucleotide sequence that is complementary to a nucleotide sequence of the docking strands and that is 8, 9 or 10 nucleotides in length. In some embodiments, the fluorescently-labeled imager strands are 8, 9 or 10 nucleotides in length.

In some embodiments, the docking strands are removed from the target proteins or the antibodies are dissociated from the target proteins.

In some embodiments, the method further comprises attaching a second type of docking strands to particular amino acids of the captured target proteins, and repeatedly contacting the captured target protein with a second set of fluorescently-labeled imager strands that transiently bind to the second set of docking strands until the location of the particular amino acids within the captured target protein is determined, thereby obtaining a partial amino acid sequence of the captured target protein.

In some embodiments, the particular amino acids are amine-containing amino acids. In some embodiments, the second set of docking strands are attached to the amine-containing through an NHS-ester or an imidoester. In some embodiments, the particular amino acids are lysines. In some embodiments, the second set of docking strands are attached to the lysines through an NHS-ester or an imidoester.

In some embodiments, the particular amino acids are sulfhydryl-containing amino acids. In some embodiments, the second set of docking strands are attached to the sulfhydryl-containing amino acids through a maleimide group, a haloacetyl group, or a pyridyldisulfide. In some embodiments, the particular amino acids are cysteines. In some embodiments, the second set of docking strands are attached to the cysteines through a maleimide group, a haloacetyl group, or a pyridyldisulfide.

In some embodiments, the particular amino acids are carboxyl-containing amino acids. In some embodiments, the second set of docking strands are attached to the carboxyl-containing amino acids through a carbodiimide. In some embodiments, the particular amino acids are aspartic acids. In some embodiments, the second set of docking strands are attached to the aspartic acids through a carbodiimide. In some embodiments, the particular amino acids are glutamic acids. In some embodiments, the second set of docking strands are attached to the glutamic acids through a carbodiimide.

In some embodiments, the captured target protein is denatured, stretched, and immobilized on the substrate. In some embodiments, the target protein is denatured using a denaturant selected from the group consisting of SDS, detergent (e.g., Triton X-100), organic solvents (e.g., ethanol), acids and bases (e.g., sodium bicarbonate, acetic acid). In some embodiments, the target protein is denatured using SDS.

In some embodiments, binding partner is specific for the target protein. In some embodiments, the binding partner is specific for a complex that comprises the target protein or for another protein that binds to the target protein.

In some embodiments, the fluorophore of the probe is photobleached when the probe is immobilized.

In some embodiments, the fixed cell or tissue is imaged using optical astigmatism imaging, optionally in combination with highly inclined and laminated optical sheet (HILO) illumination. In some embodiments, the fixed cell or tissue is imaged using a spinning disk confocal laser microscope.

Another aspect of this disclosure provides method for obtaining partial sequence information from a target protein, comprising (1) denaturing and elongating a protein,
(2) attaching docking strands to particular amino acids in the protein,
(3) capturing the protein on a substrate,
(4) repeatedly contacting the captured protein with fluorescently-labeled imager strands that transiently bind to the docking strand, and
(5) imaging the substrate, thereby locating the particular amino acids in the protein.

In some embodiments, the protein is modified with a click chemistry reacting group prior to or at the same time as docking strands are attached. Examples of click chemistry groups useful in this regard are known in the art and include but are not limited to azide, DBCO, alkynes, and the like. In some embodiments, the click chemistry reacting group is trans-cyclooctene (TCO). In some embodiments, the substrate comprises a plurality of counter-acting click chemistry groups. In some embodiments, the counter-acting click chemistry groups are 1,2,4,5-tetrazine (TZ).

In some embodiments, the protein is captured on the substrate in an electric field.

In some embodiments, the protein is denatured, stretched, and immobilized on the substrate. In some embodiments, the protein is denatured using a denaturant selected from the group consisting of SDS, detergent (e.g., Triton X-100), organic solvents (e.g., ethanol), acids and bases (e.g., sodium bicarbonate, acetic acid). In some embodiments, the target protein is denatured using SDS. In some embodiments, the protein is denatured and/or elongated using an amphiphilic agent.

In some embodiments, the particular amino acids are amine-containing amino acids. In some embodiments, the docking strands are attached to the amine-containing through an NHS-ester or an imidoester. In some embodiments, the particular amino acids are lysines. In some embodiments, the docking strands are attached to the lysines through an NHS-ester or an imidoester.

In some embodiments, the particular amino acids are sulfhydryl-containing amino acids. In some embodiments, the docking strands are attached to the sulfhydryl-containing amino acids through a maleimide group, a haloacetyl group, or a pyridyldisulfide. In some embodiments, the particular amino acids are cysteines. In some embodiments, the docking strands are attached to the cysteines through a maleimide group, a haloacetyl group, or a pyridyldisulfide.

In some embodiments, the particular amino acids are carboxyl-containing amino acids. In some embodiments, the docking strands are attached to the carboxyl-containing amino acids through a carbodiimide. In some embodiments, the particular amino acids are aspartic acids. In some embodiments, the docking strands are attached to the aspartic acids through a carbodiimide. In some embodiments, the particular amino acids are glutamic acids. In some embodiments, the docking strands are attached to the glutamic acids through a carbodiimide.

In some embodiments, the imager strands specific for a particular amino acid are contacted to the protein and imaged consecutively. In some embodiments, the imager strands for different amino acids are contacted to the protein consecutively, optionally wherein different amino acids are imaged consecutively or simultaneously.

In some embodiments, the location of the particular amino acids is determined with a 5 nm resolution.

In some embodiments, the docking strands comprise a photo-cleavable linker, and optionally the docking strands are removed by ultraviolet irradiation once imaging based on the particular amino acid is complete.

Another aspect provides a method for labeling a target protein in a cell, comprising (1) labeling microtubules in a fixed cell with a microtubule-specific binding partner conjugated to a docking strand,
(2) repeatedly contacting the fixed cell or tissue with fluorescently-labeled imager strands that transiently bind to the docking strand and imaging the fixed cell, thereby locating the position of microtubules within the fixed cell, optionally washing away unbound or transiently dissociated imager strands
(3) contacting the fixed cell with nucleic acid probes that specifically and transiently bind to docking strands, wherein the probes comprise a photocrosslinker or a photocleavable linker, a fluorophore and a conjugation handle, (4) detecting binding of the probe to a particular (or user defined) location on the microtubule, and (5) irradiating the fixed cell to immobilize the probe to the particular (or user defined) location on the microtubule, when the only binding detected is the probe bound to the microtubule at the particular (or user defined) location.

In some embodiments, the microtubule is a plurality of microtubules (such as a microtubule network).

In some embodiments, the contacting, detecting and irradiating steps are repeated until probes are immobilized to the microtubule at a plurality of particular (or user defined) locations.

In some embodiments, the plurality of particular (or user defined) locations comprises particular (or user defined) locations that are 20 nm apart from each other along the length of the microtubule.

Another aspect provides a method for locating a target in a cell, comprising (1) labeling a target in a fixed cell with a binding partner conjugated to a docking strand, wherein the target is introduced into the cell prior to labeling or the target is naturally occurring in the cell, (2) repeatedly contacting the fixed cell with fluorescently-labeled imager strands that transiently bind to the docking strand and imaging the fixed cell, thereby locating the position of the target within the fixed cell, (3) contacting the fixed cell with nucleic acid probes that specifically and transiently bind to docking strands, wherein the probes comprise a photocrosslinker or a photocleavable linker, a fluorophore and a conjugation handle, (4) detecting binding of the probe to the target, optionally wherein the target is located in and only in a select region of the fixed cell, (5) irradiating the fixed cell to immobilize the probe to the target, only when the binding is detected in a select region of the fixed cell, and (6) optionally imaging the fixed cell by detecting signal from the immobilized probe.

Another aspect provides a method for locating a target in a cell, comprising (1) introducing into a fixed cell a target conjugated to a docking strand, (2) repeatedly contacting the fixed cell with fluorescently-labeled imager strands that transiently bind to the docking strand, and imaging the fixed cell, thereby locating the position of the target within the fixed cell, (3) contacting the fixed cell with nucleic acid probes that specifically and transiently bind to docking strands, wherein the probes comprise a photocrosslinker or a photocleavable linker, and a fluorophore and a conjugation handle, (4) detecting binding of the probe to the target, optionally wherein the target is located in and only in a select region of the fixed cell, (5) irradiating the fixed cell to immobilize the probe to the target, only when the binding is detected in a select region of the fixed cell, and (6) optionally imaging the fixed cell by detecting signal from the immobilized probe, wherein the target is a synthetic nucleic acid nanostructure.

A synthetic nucleic acid nanostructure, as used herein, refers to a nanostructure, typically of defined shape and size, that is generated in vitro using hybridization techniques such as but not limited to DNA origami and the like. The defined shape and size of the nanostructure permits its use as a control or as a fiducial in methods directed towards imaging and/or modifying other targets such as but not limited to naturally occurring proteins for example.

Another aspect provides a method for locating a target on a cell, comprising (1) attaching to the surface of a cell a target conjugated to a docking strand, (2) repeatedly contacting the cell with fluorescently-labeled imager strands that transiently bind to the docking strand, and imaging the cell, thereby locating the position of the target(s) on the cell, (3) contacting the cell with nucleic acid probes that specifically and transiently bind to docking strands, wherein the probes comprise a photocrosslinker or a photocleavable linker, and a fluorophore and a conjugation handle, (4) detecting binding of the probe to the target, optionally wherein the target is located in and only in a select region on the surface of the cell, (5) irradiating the cell to immobilize the probe to the target, only when the binding is detected in a select region of the surface of the cell, and (6) optionally imaging the cell by detecting signal from the immobilized probe, wherein the target is a synthetic nucleic acid nanostructure.

Another aspect provides a method for labeling and optionally selectively activating and/or deactivating an ion channel, comprising (1) forming a liposome comprising an ion channel conjugated to a docking strand, (2) repeatedly contacting the liposome with fluorescently-labeled imager strands that transiently bind to the docking strand and imaging the liposome, thereby locating the position of the ion channels on the surface of the liposome, (3) contacting the liposome with nucleic acid probes that specifically and transiently bind to docking strands, wherein the probes comprise a photocrosslinker or a photocleavable linker, a fluorophore and a lumitoxin moiety, (4) detecting binding of the probe to an ion channel that is located in and only in a select region on the surface of the liposome, and (5) irradiating the liposome to immobilize the probe to ion channel in the select region on the surface of the liposome.

Another aspect provides a method for labeling and optionally selectively activating and/or deactivating an ion channel, comprising (1) attaching a docking strand to a plurality of ion channels on an cell, (2) repeatedly contacting the cell with fluorescently-labeled imager strands that transiently bind to the docking strand and imaging the cell, thereby locating the position of the ion channels on the cell, (3) contacting the cell with nucleic acid probes that specifically and transiently bind to docking strands, wherein the probes comprise a photocrosslinker or a photocleavable linker, a fluorophore and a lumitoxin moiety, (4) detecting binding of the probe to an ion channel that is located in and only in a select region on the surface of the cell, and (5) irradiating the cell to immobilize the probe to ion channel in the select region on the surface of the liposome, only when the probe is bound to an channel in a select region.

In some embodiments, the ion channels in the cell are genetically engineered to comprise a protein tag.

Another aspect provides a method for labeling and optionally selectively activating and/or deactivating an ion channel, comprising (1) genetically engineering a cell to express a plurality of ion channels each having a protein tag, (2) attaching a docking strand to the ion channels via the protein tag, (3) repeatedly contacting the cell with fluorescently-labeled imager strands that transiently bind to the docking strand and imaging the cell, thereby locating the position of the ion channels on the cell, (4) contacting the cell with nucleic acid probes that specifically and transiently bind to docking strands, wherein the probes comprise a photocrosslinker or a photocleavable linker, a fluorophore and a lumitoxin moiety, (5) binding the probes the ion channels thereby attaching a lumitoxin moiety to a plurality of ion channels, and (6) removing the lumitoxin moiety from ion channels in a select region.

It should be understood that in any of the foregoing methods, the region of interest or user defined location is or is located within a diffraction limited region. In some embodiments, the entire region including the region of interest is irradiated. In other embodiments, only the region of interest is irradiated, that the diffraction limited region is irradiated. This may be accomplished using for example a DMD array.

In yet another aspect, disclosed herein is a method comprising contacting a plurality of transiently binding nucleic acid probes to their respective targets wherein the targets are immobilized on a substrate, detecting a binding event in a select region or set of select regions within a diffraction limited region of the substrate, and irradiating the diffraction limited region of the substrate, wherein the probes comprise a photocrosslinker. In one embodiment, the photocrosslinker is 3-cyanovinylcarbazole. In one embodiment, the diffraction limited region of the substrate is irradiated with 366 nm to 405 nm light for less than 1 second or less than 0.5 seconds. The probe may be of a sequence and length sufficient to achieve transient binding to the target. Examples of probe sequence motifs are provided herein.

In another aspect, disclosed herein is a method comprising contacting a plurality of transiently binding nucleic acid probes to their respective targets wherein the targets are immobilized on a substrate, detecting a binding event in a select region within a diffraction limited region of the substrate and irradiating diffraction limited region of the substrate, wherein the probes have a hairpin secondary structure and have a photocleavable linker or spacer along their length (such that breakage of the linker or spacer will induce a covalent break in the chain). In one embodiment, the photocleavable linker comprises 1-(2-nitrophenyl)ethyl. In some embodiments, the diffraction limited region of the substrate is irradiated with light having a wavelength of equal or less than 405 nm, optionally for less than 1 second or less than 0.5 seconds. The probe may comprise a toehold (i.e., a nucleotide sequence that is single-stranded prior to binding to the target and from which binding to the target begins). The toehold may have characteristics similar to those of standard "Points Accumulation for Imaging in Nanoscale Topography (PAINT)" probes including particular binding energy (when bound to target) which in turn is dependent on sequence and length.

In the aforementioned aspects, the irradiating step occurs if the binding event in the select region is the only binding event in the entire diffraction-limited region. In this respect, if the binding event triggers the irradiation step (or event) it may be referred to herein as a "sole" binding event to mean that it is the only binding event in the diffraction-limited region. If other binding events are detected simultaneously with the binding event in the select region, irradiation does not occur. In this manner, probes are attached only to the select region and not other regions within the diffraction limited region.

The transient nature of binding between the probe and target dictates the nature of the photocrosslinker and photocleavable linker to be used, in some instances. The photocrosslinker and photocleavable linker typically can be activated with short laser pulse durations at power densities in the range of ~1 W/cm$^2$ (or less) to kilowatts/cm$^2$, which in turns means they can be activated in very short time frames with standard and inexpensive lasers commonly used for biological imaging applications such as STochastic Optical Reconstruction Microscopy (STORM) superresolution imaging. This is important since the binding between the probe and the target only occurs for a short time period and one may wish to avoid radiation damage of the substrate being patterned or previous patterned probes or their cargo. Activation of the photocrosslinker and photocleavable linker, as used herein, intends formation of a covalent adduct and cleavage of a bond, respectively.

The select region of the substrate to be patterned may be smaller than the diffraction limited region. The select region of the substrate to be patterned may (or may not) have features or sections that locally have an area (or volume) that are smaller than the area (or volume) of the diffraction limited region to which they correspond. In some embodiments, the select region(s) to be patterned is not smaller than a diffraction limited region, and instead it may contain features (which may or may not connected) which are smaller than the immediate diffraction limited region. Whether a probe is located in an arbitrary two- or three-dimensional select region (which may be referred to herein as a stencil) is determined based on the precision and accuracy with which the probe can be observed using superresolution microscopy. Accordingly, patterning stencils with geometrically defined features at size scales below the diffraction limit may be used.

It is to be understood that the irradiation step occurs shortly after the desired binding event is detected. The time between detection and irradiation may be on the order of milliseconds. The method may be automated and may employ a CCD or EMCCD camera to detect the binding event within the diffraction limited region. The method may also employ a laser spot illuminator or a Digital Micromirror Device (DMD) array. If a DMD array is used, multiple diffraction limited regions may be monitored and patterned simultaneously or in parallel.

In some embodiments, the probes further comprise a fluorophore. In some embodiments, the fluorophore is ATTO 655, Alexa 647, or other bright fluorophore. As used herein, a "bright fluorophore" is one that emits a sufficient number of photons such that the CCD or EMCCD camera is able to detect single binding events. In some embodiments, the fluorophore is one that releases at least or about $10^4$-$10^6$ photons. In some embodiments, Trolox, b-mercaptoethanol (BME), L-cysteine methyl ester (L-Cys-ME), cyclooctatetraene (COT), n-propyl gallate, 1,4-diazabicyclo[2.2.2]octane (DABCO), or mercaptoethylamine (MEA), and other agents may be present in the imaging buffer to redox permanent photobleaching rates for dyes (e.g., by scavenging Reactive Oxygen Species (ROS) like singlet oxygen) and thus increase dye photon output and localization precision). Typically, the excitation and emission wavelengths of the fluorophores used are outside of the range of wavelengths that are used to activate the photocrosslinker or photocleavable linker. In some embodiments, the probes further comprise a functional group or a moiety. In some embodiments, the functional group or the moiety is a chemical handle. In some embodiments, the functional group or the moiety is biotin, avidin, or a nanoparticle. In some embodiments, the functional group or the moiety is an alkyne or azide (e.g., used for "click chemistry"). In some embodiments, the functional group or moiety is used to attach a cargo to the substrate. The cargo may be chemical compounds typically used in lithography in the semi-conductor industry. An example of such a chemical compound is PDMS or PMMA.

In some embodiments, the select region of the substrate is a select area or a select volume of the substrate. The select region may be a region or a pattern predetermined by an end user (e.g., a region the end user wishes to deposit a particular cargo of interest in or on). The region may be an area or a volume. The pattern may be two-dimensional or three-dimensional. In the latter context, the substrate may be a cell or other three dimensional moiety.

In some instances, the diffraction-limited region comprises a plurality of targets bound relatively uniformly throughout its area or volume. In this way, a substrate may be prepared to comprise targets bound to one or more of its surfaces and one of more of its volumes, and may be treated to create super-resolution patterns as provided herein. The targets bound to the substrate may be identical to each other or they may be different. If different, there may be 2-1000 populations of targets attached to the substrate. Any given diffraction limited region may comprise 1-1000 populations of targets. In some instances, the targets may provided as oligonucleotides bound to colloidal gold particles (e.g. 5 nm Au nanoparticles) or iron oxide nanoparticles with catalytic properties.

In some embodiments, wherein probes bound to target outside of the select region of the substrate are removed (e.g., washed away upon dissociation from their respective targets).

The foregoing methods may be used to create patterns of moieties of interest, for example by conjugating the moiety of interest to the probe before or after binding to the target. As described herein, the patterns may have super-resolution dimensions (i.e., dimensions that are less than the resolution limit of an optical detection system). For example, the patterns may have features or components with dimensions that are less than the diffraction limited resolution (and are thus located within a diffraction limited area, which may be for example a few hundred nanometers in one dimension).

These and other aspects and embodiments of the invention will be described herein and are considered to be part of this disclosure.

BRIEF DESCRIPTION OF DRAWINGS

FIGS. 9A-E illustrate Action-PAINT in cells. (A,B) Preliminary work of 2D (A) and 3D (B) DNA-PAINT imaging of cellular targets;[32] (C,D) 3D-Action-PAINT in situ demonstration. (C) A specified vertex of the 3D nanostructures (immobilized on a cell surface) will be modified with a unique DNA molecule using 3D-Action-PAINT. (D) Microinjected 3D nanostructures will be site-specifically modified with 3D-Action-PAINT throughout a whole cell volume using a spinning disk confocal system. (E) Action-PAINT to label a microtubule network tagged with DNA coupled antibodies at an interval of 20 nm.

DETAILED DESCRIPTION

Figure 2A:
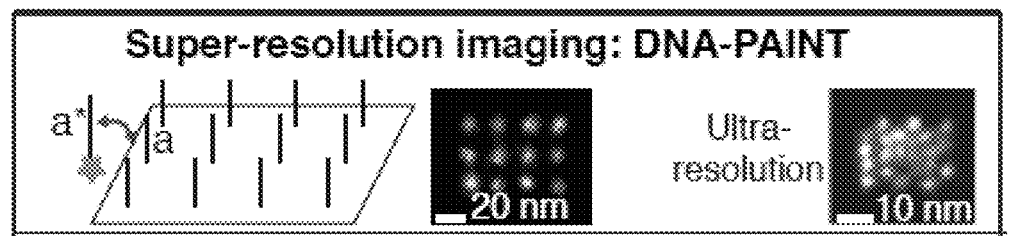
FIGS. 2A-D illustrate super-resolution labeling (Action-PAINT).

Super-resolution imaging methods are known in the art and include but are not limited to Stochastic Optical Reconstruction Microscopy (STORM)[1] and Points Accumulation for Imaging in Nanoscale Topography (PAINT)[2,3]. The super-resolution labeling methods provided herein are based in part on such super-resolution imaging methods (FIG. 2A). Briefly, in DNA-PAINT, the sample is modified with short (8- to 9-nt) "docking strands" (strand α in FIG. 2A), and the solution contains fluorophore (depicted as a star) labeled "imager strands" (a*). An imager strand can transiently bind to a docking strand, making it bright under total internal reflection (TIR) imaging. The repetitive, transient binding of imager strands stochastically switches the docking strands between bright and dark states, and enables super-resolution imaging of these docking strands by sequentially and precisely localizing one docking strand at a time. DNA-PAINT can be used to visualize proteins in fixed cells with sub 10-nm resolution[32]. High-density, ultra-resolution images have also been obtained, involving docking strands spaced only 5 nm apart on a DNA nanostructure (FIG. 2A, right).

Figure 2B:
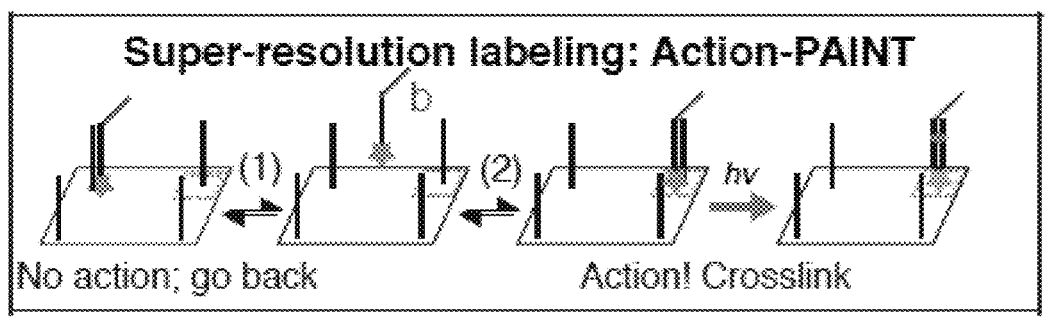

To achieve super-resolution labeling (FIG. 2B), an imager strand is modified for example with a photo-crosslinker and a conjugation handle (b segment in FIG. 2B). When the imager strand is present in a desired location under DNA-PAINT (i.e. binds to the docking strand in the region of interest [depicted with box]; case (2) in FIG. 2B), the imager strand is photo-crosslinked to the docking strand, and the docking strand in the region of interest is then modified with the conjugation handle. However, when the imager strand lands outside the region of interest (case (1) in FIG. 2B) crosslinking is not triggered. This process is referred to as "Action-PAINT" in this disclosure. These methods can be carried out in the context of nucleic nanostructures, cells and tissues including fixed cells and tissues, and live cells and cell membranes.

Figure 2C:
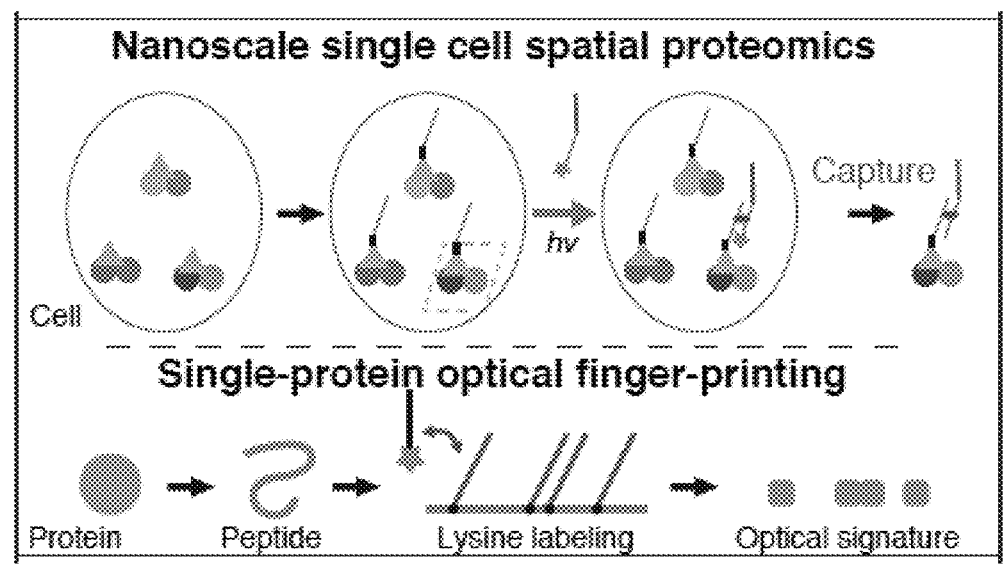
Figure 2D:
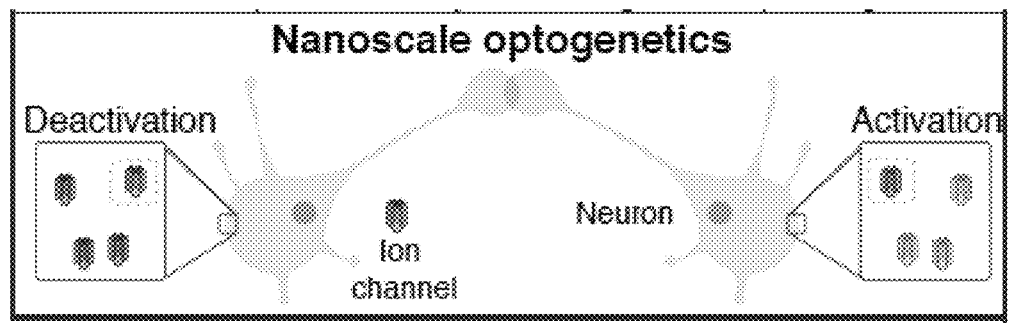

Action-PAINT provides a broadly enabling platform to achieve nano-scale labeling and manipulation of molecular targets in cells. Action-PAINT can be used for nanoscale single-cell spatial proteomics, where particular protein and their associated partners can be specifically captured and labeled at a user-specified location (FIG. 2C, top). These proteins can then be identified using a single-protein fingerprinting method (FIG. 2C, bottom) whereby each protein is denatured and stretched, particular amino acids (e.g. lysine)

are labeled with DNA docking strands, and ultra-high resolution DNA-PAINT will generate an optical geometrical signature for protein identification. Action-PAINT can also be used for nanoscale optogenetics, where molecular perturbing agents (e.g. lumitoxin which blocks ion channels) will be delivered to user-specified ion channels on a neuron, thereby enabling specific optical activation/de-activation of ion-channels with nanometer precision (FIG. 2D). Action-PAINT can also be used for site-specific target labeling and purification, perturbation and cargo loading on site-specific targets, etc.

This disclosure provides an integrated super-resolution visualization and labeling method. The method is based on super-resolution visualization of transient binding of short oligonucleotides, and real-time site-specific activation of these oligonucleotides for chemical modification. Super-resolution imaging using DNA-PAINT[3] has been previously demonstrated with ultra-high spatial resolution (<5 nm) and ultrahigh multiplexing power (up to 10 colors).[32] This disclosure extends such methods by integrating real-time visualization and activation. The activation step is achieved via photo-reactive chemistry, including the use of short oligonucleotides comprising photo-cleaving and photo-crosslinking bases.

Thus, as will be understood from the foregoing, in certain super-resolution imaging methods, probes bind transiently, rather than stably, to their targets. Images may be acquired continuously (e.g., using time-lapse techniques) or serially (with for example subsequent alignment and overlaying), optionally with drift correction if the substrate (or stage) moves during image acquisition. Methods for drift correction are known in the art. The resultant images can then be used to define probe binding and thus target location.

The transient nature of probe binding allows an end user to discern more target locations, including of particular importance target locations that are located within a resolution limit for a given optical detection system. Thus, two target locations that are separated from each other by less than the resolution limit of the optical detection system being used would not be discernible as two separate locations using conventional stable binding probes. However, if transiently binding probes are used, there is a greater probability that at any given time one of the two target locations will not be bound by its respective probe. Images can then be obtained when only a single target location is bound to its respective probe, and the compilation of these images will render the two target locations as separate locations.

The invention employs the super-resolution imaging techniques and builds upon them to pattern a substrate at a super-resolution level. The ability to pattern a substrate at super-resolution dimensions has various applications including in lithography. Moreover, since each probe may be loaded with a diversity of cargo, the invention facilitates patterning of various cargos also.

Probes

Probes to be used in the methods of the invention may be any moiety able to bind to a target of interest. In some instances, the probe may bind specifically to target (i.e., it has higher affinity or effectively sole affinity for one target).

The targets may be nucleic acids, proteins, and other biological and non-biological entities. In some embodiments, the targets (or docking sites) may be within 200 nm of each other on the substrate. The probes may be nucleic acids (e.g., such as oligonucleotides and including aptamers), proteins (e.g., such as antibodies or antibody fragments), and the like. In certain embodiments, the targets and probes are nucleic acids, and more particularly oligonucleotides.

In important embodiments, the probes are nucleic acids that are transiently bound to their targets at room temperature. In some embodiments, the probe is 7-12 nucleotides in length. In some embodiments, the probe is about 9 nucleotides in length. In some embodiments, the probe is fluorescently labeled. When oligonucleotides of this length are used, the strength of binding between the oligonucleotide and its target is reduced and accordingly they are more likely to dissociate than are longer oligonucleotides bound to their targets. At room temperature, oligonucleotides and target regions that are about 8 or about 9 nucleotides in length associate with each other only transiently. As will be understood in the art, at higher temperatures, the length of the oligonucleotide and the target region will typically be increased in order to achieve the same association/dissociation kinetics. Such lengths may range, without limitation, from about 5 nucleotides to 30 nucleotides, or from about 7 nucleotides to about 25 nucleotides, or from about 9 nucleotides to about 21 nucleotides. The probe may be referred to herein as an imager strand and the target may be or may be conjugated to a docking strand, which is complementary to the imager strand. Accordingly, the target may be a docking strand or it may be another agent of interest that has been modified to comprise a docking strand.

The probe and target may be designed based on the binding energy of their interaction. Thus, in some instances, the binding interaction between the probe and the target may be defined as having a binding energy of $\Delta G$ at 25° C. of about −6.92 kcal/mol. The $\Delta H$ (enthalpy) may be about −58 kcal/mole and the $\Delta S$ (entropy) may be about −0.171 kcal/(K·mol). These binding energies presume a binding environment (e.g., a hybridization environment) comprising about 50 mM to about 1 M NaCl. If the binding is occurring at a higher temperature (e.g., body temperature), then the binding energy $\Delta G$ (at 37° C.) is about −4.86 kcal/mol. Accordingly, the probes and targets may be designed to achieve binding energies at or about these amounts.

It is to be further understood that the probe may comprise or consist of a nucleic acid and the target may comprise or consist of a nucleic acid. For example, the probe may be a conjugate of a nucleic acid and another moiety such as a protein. In nucleic acid facilitates interaction and immobilization on the substrate. Alternatively, if the probe is a nucleic acid having a chemical handle, then such chemical handle may be used post-immobilization in order to attach another moiety such as for example a protein at the particular region on the substrate.

The probe will be further modified as described herein with for example a functional group or a moiety. The nature of the functional group or moiety will depend upon the particular application. Examples include binding partners such as biotin and avidin, nanoparticles or microparticles, other forms of cargo, and chemical groups such as alkynes or azides and the like.

Patterning Methods

Various aspects of this disclosure transform super-resolution imaging methods, such as Stochastic Optical Reconstruction Microscopy (STORM)[1] and Points Accumulation for Imaging in Nanoscale Topography (PAINT)[2,3], into high-throughput lithographic tools that allow for patterning of molecules at the same resolution at which they can be optically resolved.

Photocrosslinking Methods

This disclosure provides, in one aspect, methods, products and devices for crosslinking PAINT probes. In some embodiments, the probes are photocrosslinked. In some embodiments, such probes are crosslinked, including photocrosslinked, to binding partners such as complementary binding partners.

In some embodiments, the probes comprise a crosslinker such as a photocrosslinker. The crosslinker, including the photocrosslinker, may be located at an end of a probe (e.g., a 5' end or a 3' end) or it may be at an internal position. In some embodiments, the crosslinker, including the photocrosslinker, may be located near or at the center of probe (e.g., relative to its length). The probe may comprise one or more crosslinkers.

In some embodiments, the crosslinker is a photocrosslinker. An example of a photocrosslinker that may be used in accordance with this disclosure is 3-cyanovinylcarbazole. Other crosslinkers, including photocrosslinkers (e.g., cinnamate, halogenated bases such as 5-Bromo dU, psoralen), are known in the art and may be used in other embodiments in keeping with this disclosure.

One aspect combines a super-resolution imaging technique such as PAINT[2,3] with a crosslinking technique such as photochemical crosslinking with 3-cyanovinylcarbazole nucleoside ($^{CNV}k$) chemistry[4-7]. This combination is then further combined with a light source such as for example a laser spot illuminator such as for example one operating at ≈20 Hz[8], or a Digital Micromirror Display (DMD) array with for example about $10^3$ to $10^6$ individually programmable mirrors (for massively parallel spot illumination)[8-10]. By integrating these elements, a fast laser-based feedback system is created that utilizes CCD camera input to permanently immobilize ($^{CNV}K$) labeled probes such as PAINT probes that are transiently occupying docking sites placed by Random Sequential Adsorption/Addition (RSA)[11-13] on a two-dimensional surface, or in a three-dimensional volume.

The docking positions typically are present within an area or volume of the patterning substrate that is within the Total Internal Reflection Fluorescence (TIRF) evanescent field observable with the CCD camera used for fluorophore localization.

A "typical" CCD camera field of view (FOV) is around ≈50 μm$^2$ (e.g., with an Andor iXon 897 EMCCD camera[14] with its array of 512×512 pixels), and can be reasonably scaled up to ≈150 μm$^2$ to ≈200 μm$^2$ area using a ≈4 megapixel (2048×2048 pixel array) Orca-Flash 4.0 V2 Scientific CMOS CCD[15]. These FOVs however can be scaled-up using some existing techniques including calibration and correction routines for Photo-Response Non-Uniformity (PRNU) that allow for the use of lower objectives (i.e., fewer pixels per diffraction limited area)[16] as well as advances in CCD camera detector quantum efficiencies and pixel densities. These should provide significant opportunity for scaling of workable detector FOVs for high resolution single-molecule localization and patterning.

Concerning the matter of patterning in a three-dimensional volume, the extent along the z-axis of the focal plane that can be patterned (i.e., the accessible "depth-of-field"), and the resolution achievable for patterning, is dependent on how well fluorescent objects can be resolved by various three-dimensional super-resolution methods. To this end, by applying Rafael Piestun's Double-Helical Point Spread Function (DH-PSF)[17] to three-dimensional super-resolution imaging techniques such as STORM (or the protein variant of STORM, Photoactivated Localization Microscopy (PALM)[18]), Moerner et al. was able to demonstrate isotropic ≈10 nm to ≈20 nm resolution for single fluorescent molecules along the x-, y-, and z-axes over a ≈2 μm depth-of-field[19,20] and to also extract (z, θ, φ) dye orientation parameters within standard deviations of ≈10 degrees[21]. This exceeds the ≈600 nm depth-of-field and ≈1 μm depth-of-field for fluorescent dye localizations achieved by astigmatism[22] and multiplane[23,24] methods, respectively, and generally exceeds the 3-space resolution of either method over short or long depth-of-field ranges[25-27]. Accordingly, these processes may be used in the methods of the disclosure.

Certain methods of the disclosure use CCD camera input to guide a laser feedback system in order to "freeze" stochastic fluorescent probe binding interactions, thereby allowing an end user to walk up an entropic gradient through the buildup of arbitrarily complex patterns of molecules or particles attached to fluorophores. Using this feedback protocol for fluorescent probe localizations, randomly flashing a laser to lock probes in place will cause uniform and random patterning over the set of potential probe docking sites.

The ($^{CNV}k$)[4-7] nucleoside may be incorporated in a PAINT[2,3] probe sequence, preferentially near the center of a given probe to maximize thermodynamic stability. Preferably a pyrimidine base (optimally a thymine, uracil, or methylcytosine)[4-7] is present on the modified probe's docking site as the Watson-Crick complement of the nucleotide immediately upstream of the ($^{CNV}k$) insertion on the probe.

The ($^{CNV}k$) crosslinking reaction is sensitive to the nearest-neighbor nucleotides flanking the insertion site[4,7]. In the following nucleotide context

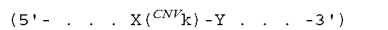
(5'- . . . X($^{CNV}k$)-Y . . . -3')

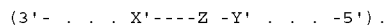
(3'- . . . X'----Z -Y' . . . -5').

X' is the pyrimidine base that covalently crosslinks with the ($^{CNV}K$) group, the Z nucleoside lies opposite to the ($^{CNV}k$) duplex insertion but does not participate directly in the crosslinking reaction, while the Y/Y' Watson-Crick nucleotide pair influences the crosslinking reaction via stacking interactions with the ($^{CNV}k$)/Z pseudo-basepair. Provided that X'=T or U, which are optimal choices for pyrimidine base crosslinking targets, the choice of Z and Y may have less influence[4,7]. A methylated cytosine can serve as a similarly effective crosslinking target (i.e., X'=Cm)[7].

For a specific X'=T example[4,7], the following pair of hybridized oligonucleotides gives ≈50% photocrosslinking yields after <1 second of irradiation at ≈366 nm with a power density of ≈1.5 W/cm2 using a UV LED lamp-based light source[4,7]:

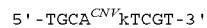
5'-TGCA$^{CNV}$kTCGT-3'

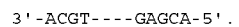
3'-ACGT----GAGCA-5'.

Thus, a probe may comprise or consist of the following sequence:

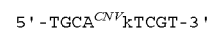
5'-TGCA$^{CNV}$kTCGT-3' and the corresponding target may comprise or consist of the following sequence:

3'-ACGT--GAGCA-5'.

The energy approximations for such a probe-target pair are as follows:
ΔH(0.01 M to 1 M NaCl):: −49.4 kcal/mol,
ΔS(1 M NaCl):: −0.134 kcal/(K*mol),
ΔG(1 M NaCl, 25° C.):: −9.57 kcal/mol, and
ΔG(1 M NaCl, 37° C.):: −7.96 kcal/mol.

In some embodiments, to make the probe more suitable for PAINT, the ΔG values can be altered by manipulating the monovalent ion concentration of the solution. For example, the concentration of NaCl monovalent ions can be decreased to lower the thermostability of this sequence, or alternatively, the NaCl concentration can be increased to compensate for destabilizing effects due to the introduction of the ($^{CNV}$k) group.

Kinetic Trapping Via 1-(2-nitrophenyl)Ethyl Photocleavage

Other aspects of this disclosure are variations of the photocrosslinking embodiments described herein. In one such variation, photocleavable spacers such as 1-(2-nitrophenyl)ethyl photocleavable spacers[31] (commercially available from Ambergen) are inserted in hairpin variants of PAINT[2,3] probes. This allows for the use of a laser-based feedback system to kinetically trap stochastic PAINT probe binding interactions in place at desirable locations and/or at desirable times. The photocleavable spacer chemistry is an alternative to the fast and direct photocrosslinking with 3-cyanovinylcarbazole ($^{CNV}$k)[4-7] modified nucleosides.

An example of a nucleic acid that can be used in this embodiment is as follows:

(SEQ ID NO: 1)
5'-/5ATTO655N/<u>TAGATGTAT</u> GGTCTG/iSpPC/CCGGACTTTTTT

TCAATGTAT TTTTTTT GTCCGGCAGACC <u>ATACATCTA</u>

TCTTCATTA - 3' where "/5ATTO655N/" is defined as an indicator for the position of a covalently conjugated ATTO655 dye on an oligonucleotide, and "/iSpPC/" is defined as an indicator for the position of a photocleavable spacer using for example 1-(2-nitrophenyl)ethyl chemistry[31]. This probe has a length of 74 nucleotides and comprises a toehold (bolded sequence) that is 9 nucleotides in length.

Figure 1:
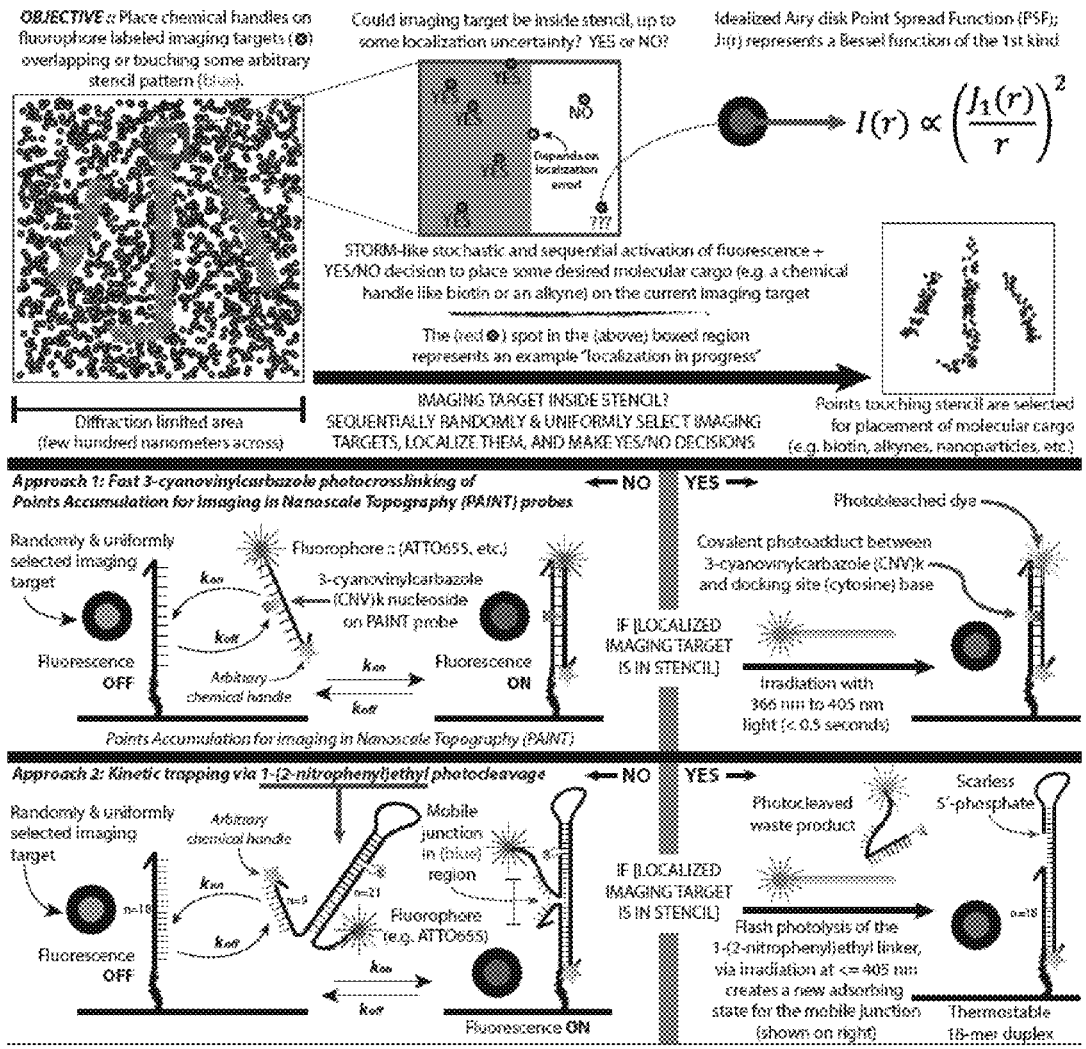
FIG. 1 illustrates various aspects and embodiments of this disclosure including the use of photocrosslinking of probes and kinetic trapping of probes via photocleavage.

Aspects and embodiments of this disclosure are illustrated in FIG. 1 which is described in greater detail below. As shown in the Figure, the methods provided herein may be used to place particular chemical handles of interest (denoted by 5 point stars in the bottom of the Figure) in a pre-determined (and potentially arbitrary) pattern on a substrate. The top of the Figure illustrates a diffraction-limited area within which an arbitrary pattern is denoted in thick "curved rectangles". The end result of the process illustrated in the Figure is the generation of a pre-determined pattern using moieties of interest as shown at in top right box.

The middle panel illustrates how the pattern can be achieved using photocrosslinking. The left panel illustrates the presence of the target on the substrate. In this instance, the target is a single stranded nucleic acid. The single stranded nucleic acid may be present on 5 nm colloidal gold particles that are distributed relatively evenly across the area, as an example. The probe is also a single-stranded nucleic acid having a fluorophore at one end and a chemical handle at the other end. It is to be understood that the chemical handle is merely representative of any functionality or moiety of interest. The probe further contains a photocrosslinker in the form of a 3-cyanovinylcarbozole. The photocrosslinker is present as part of a modified nucleoside in the oligonucleotide probe. When the probe binds to its target (typically through Watson-Crick hybridization in the case of nucleic acid targets and probes), the location of the target is apparent as a result of emission from the fluorophore on the probe. If the target is located in the pre-determined region of interest (referred to as the "stencil" in the Figure) and importantly if it is the only detected binding event at that time, then the entire region will be irradiated resulting in the formation of a covalent bond between the target and the probe only at the region of interest. In the illustrated example, a covalent photoadduct between 3-cyanovinylcarbazole and its docking site (in the form of a cytosine base) is generated. The probe is therefore immobilized via such covalent binding, as is its cargo. The irradiation also serves to photobleach the fluorophore, or alternatively irradiation closer to the fluorophore's wavelength can be used to accomplish this, so that the process can be repeated numerous times to immobilize additional probes in the region of interest without interference from previously immobilized probes. In this particular instance, photocrosslinking can be achieved by irradiating with wavelengths of 366-405 nm for less than 1 second or less than 0.5 seconds. It is to be understood that irradiation occurs only when a single binding event is detected in the diffraction limited region and that binding event is present in the region of interest. If a binding event is detected outside the region of interest, no irradiation occurs. Any probes bound to targets outside of the stencil area (or volume) are bound only transiently and thus can be removed readily via one or more washes.

It is to be understood that other photocrosslinkers and other fluorophores could be used provided the photocrosslinkers can be activated relatively quickly (and thus with relatively little energy) and the fluorophores are able to emit a sufficient number of photons to be detected in relatively short periods of time. It is therefore to be appreciated that the kinetics of probe binding, detection of probe binding (as a result of fluorophore emission), and photocrosslinker activation are all inter-related.

The probe and target may also be designed to include particular sequence motifs in order to enhance their binding and subsequent covalent interaction, as described herein.

The bottom panel illustrates how the pattern can be achieved using photocleavage. Again, the left panel illustrates the presence of the target on the substrate, similarly to the middle panel. As illustrated, the target has two regions (nucleotide sequences). One of these regions is complementary to a particular region (nucleotide sequence) on the probe near the chemical handle (referred to herein as a toehold). The other region is complementary to another particular region on the hairpin probe. The structures of the hairpin probe in its unbound and bound states are also illustrated. The hairpin probe comprises a chemical handle at one end, a fluorophore at the other end, and a photocleavable linker at an internal position. When bound to its target on the substrate (through a process that typically proceeds from the toehold interaction with the target), the location of the target is indicated by fluorescence emission from the fluorophore. If the target is in the pre-determined region of interest (the stencil) and if no other binding event is detected in the diffraction limited region, then the entire region will be irradiated resulting in the cleavage of the hairpin loop and release of a region of the probe that comprises the fluorophore. The flash photolysis of the 1-(2-nitrophenyl)ethyl linker, via irradiation at less than or equal to 405 nm, in this instance, creates a thermostable 18-mer duplex. As illustrated the release of a region of the probe creates a single-stranded region on the resultant relatively immobilized probe. As indicated in the Figure, following cleavage, the immobilized probe may have a "scarless 5' phosphate" (e.g., if a 1-(2-nitrophenyl)ethyl linker is used as indicated in the diagram) intending that such an end can be used in a ligation reaction, for example, without further modification.

The toehold sequence and length is designed such that the binding energy of the toehold is strong enough to begin the process of hybridizing the probe to the target but labile enough to still be transiently binding (so as to achieve super-resolution imaging and thus patterning as provided herein). The toehold region therefore may be in some instances about 9 nucleotides in length or less.

It is to be understood that other photocleavable linkers and other fluorophores could be used provided the photocleavable linkers can be activated relatively quickly (and thus with a short duration laser pulse with a power density of ~1 W/cm$^2$ to kilowatts/cm$^2$) and the fluorophores are able to emit a sufficient number of photons to be detected in relatively short periods of time. It is therefore to be appreciated that the kinetics of probe binding, detection of probe binding (as a result of fluorophore emission), and photocleavable linker activation are all inter-related.

Thus as will be understood in the context of this disclosure, the desirability of a binding event depends on its location (e.g., (x,y) or (x,y,z)) and its singularity in the diffraction limited region.

The methods provided herein allow an end user to place a chemical handle or marker on a select region. Once a binding event is detected in and only in the select region, the entire diffraction limited region may be irradiated thereby immobilizing the probe to the select region. The chemical handle or marker may be or may be used to attach for example a nanoparticle (for Raman spectroscopy) or a bead (for force spectroscopy) or a fluorescent particle (for FACS).

The ability to wait for a probe binding event with some desired localization in (x,y) or (x,y,z), check if the probe is alone in a diffraction limited area, and then if so, make a decision to covalently attach it to the substrate (at its binding position) with a laser, allows an end user to label moieties at specific sites below the diffraction limit. The labels may be detectable labels or they may be affinity labels, as non-limiting examples. In the lithography context, it may be desirable to place a large number of labels in a diffraction limited region in a manner that mimics standard lithographic techniques that change the chemical composition of a diffraction limited region.

In some embodiments, UV or near-UV light (e.g., 405 nm light) can be supplanted using ultrafast pico-second to femtosecond laser pulses with very high power density (e.g., using Coherent's Ti:sapphire Chameleon Ultra II system)[36]. This allows the use of "red-shifted" light (e.g., absorbing two 810 nm photons, to first order approximation, is similar to absorbing one 405 nm photon with twice the energy). Longer wavelengths can mean less damage to a sample, or background fluorescence, and can also provide deeper penetration in e.g., a tissue or a 3D polymer network.

Examples of proteins for use in the methods of this disclosure include, without limitation, antibodies (e.g., monoclonal monobodies), antigen-binding antibody fragments (e.g., Fab fragments), receptors, peptides and peptide aptamers.

As used herein, "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the VH, VL, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VH and VL domains of a single arm of an antibody, (v) a dAb fragment (Ward et al., Nature 341:544 546, 1989), which consists of a VH domain; and (vi) an isolated complementarity determining region (CDR) or (vii) a combination of two or more isolated CDRs, which may optionally be joined by a synthetic linker. Furthermore, although the two domains of the Fv fragment, VH and VL, are coded for by separate genes, they can be joined, using recombinant methods, by a synthetic linker that enables them to be made as a single protein chain in which the VH and VL regions pair to form monovalent molecules (known as single chain Fv (scFv); see, e.g., Bird et al. Science 242:423 426, 1988; and Huston et al. Proc. Natl. Acad. Sci. USA 85:5879-5883, 1988). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, "receptors" refer to cellular-derived molecules (e.g., proteins) that bind to ligands such as, for example, peptides or small molecules (e.g., low molecular weight (<900 Daltons) organic or inorganic compounds).

As used herein, "peptide aptamer" refers to a molecule with a variable peptide sequence inserted into a constant scaffold protein (see, e.g., Baines I C, et al. Drug Discov. Today 11:334-341, 2006)).

As used herein, "nucleic acid aptamer" refers to a small RNA or DNA molecules that can form secondary and tertiary structures capable of specifically binding proteins or other cellular targets (see, e.g., Ni X, et al. Curr Med Chem. 18(27): 4206-4214, 2011).

Fluorescent labels that may be used in the methods described herein include xanthene derivatives (e.g., fluorescein, rhodamine, Oregon green, eosin and Texas red), cyanine derivatives (e.g., cyanine, indocarbocyanine, oxacarbocyanine, thiacarbocyanine and merocyanine), naphthalene derivatives (e.g., dansyl and prodan derivatives), coumarin derivatives, oxadiazole derivatives (e.g., pyridyloxazole, nitrobenzoxadiazole and benzoxadiazole), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), and tetrapyrrole derivatives (e.g., porphin, phthalocyanine and bilirubin). In certain embodiments, the fluorophore is ATTO655 or Alexa 647 or other bright fluorophore (e.g., a fluorophore that emits at least $10^4$-$10^6$ photons).

In certain embodiments, the fluorophore is one capable of being reversibly or permanently photobleached.

Various aspects and embodiments, and their various applications, will be described in more detail below.

Super-resolution Imaging by DNA-PAINT

Figure 3A:
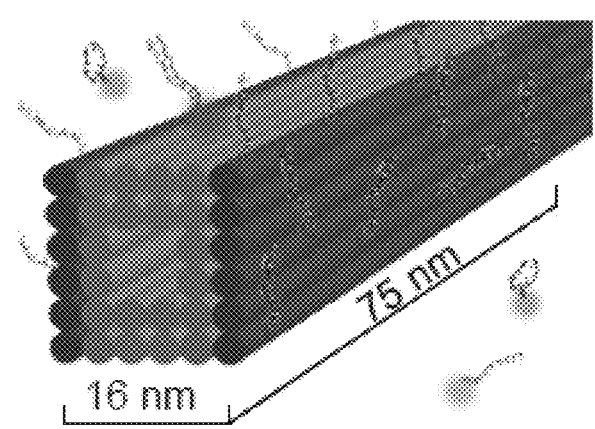
FIGS. 3A-F illustrate the DNA-PAINT concept and high spatial resolution imaging. (A-E) adapted from Rust et al.[1]
Figure 3B:
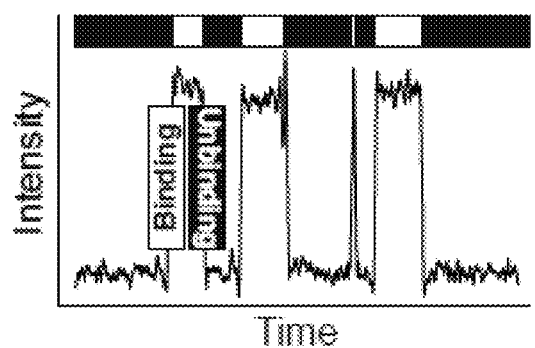
Figure 3C:
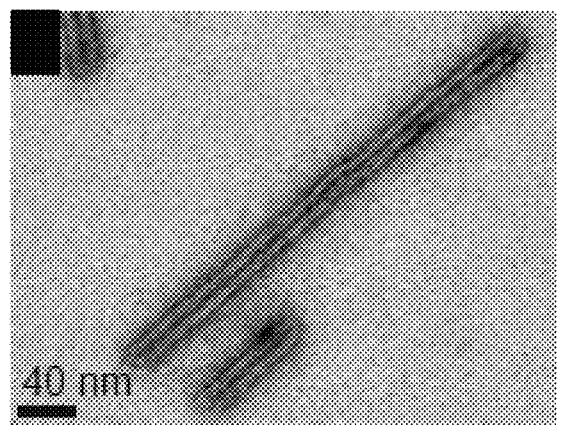
Figure 3D:
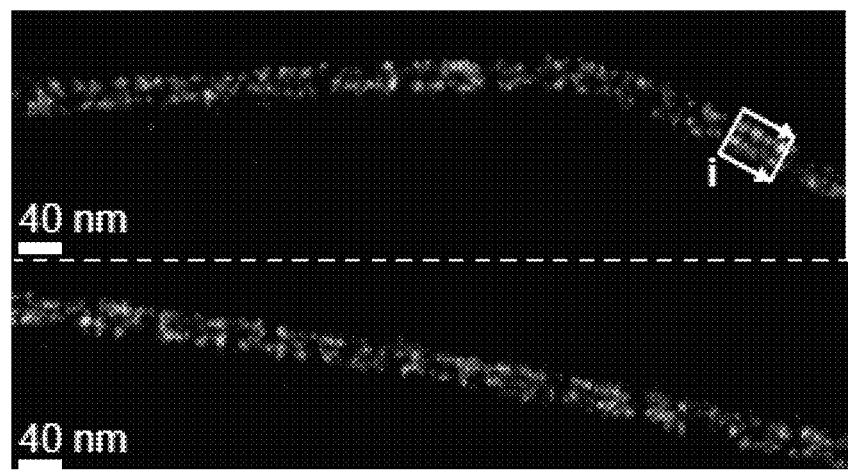
Figure 3E:
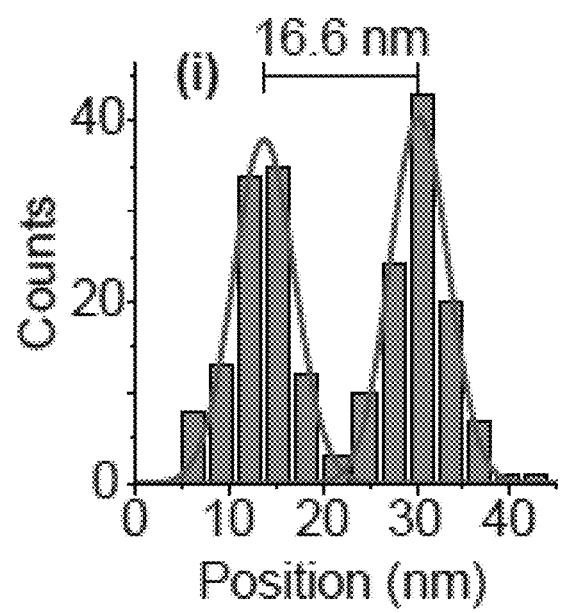

Far-field fluorescence microscopy has seen a true renaissance in recent years since the advent of methods circumventing the classical diffraction limit, i.e., super-resolution microscopy.[39-41] Super-resolution microscopy relies on the fact that molecules are 'switched' between fluorescence on-and off-states to obtain sub-diffraction image resolution[42,18,1] Point Accumulation for Imaging in Nanoscale Topography (PAINT)[2] is an easy-to-implement approach for stochastic super-resolution imaging, where imaging is performed using diffusing molecules that transiently interact with the sample. One way to implement PAINT is called DNA-PAINT,[3] where repetitive, transient binding of short fluorescently labeled oligonucleotides ('imager' strands) to complementary 'docking' strands switches molecules from dark to bright states (FIG. 3A, 3B). Only background fluorescence is observed from the sample when no imager strand is bound; upon imager strand binding, its fluorescence emission is detected using total internal reflection (TIR) or highly inclined and laminated optical sheet (HILO)[43] illumination. This integration enables specific, modular super-resolution imaging with widely adjustable fluorescence on- and off-times (set by imager strand binding strength and concentration). Recently, the resolution of DNA-PAINT was increased to ~10 nm lateral imaging resolution of in vitro synthetic DNA structures[32] (FIG. 3C-3E). Using advanced drift-correction algorithms and carefully optimized imaging conditions, high-density, ultra-resolution DNA-PAINT images have been achieved, where docking sites are spaced only ~5 nm apart (FIG. 3F). 3D imaging of synthetic nanostructures[38] and fixed cells[38] has also been demonstrated.

Action-PAINT in 2D

Figure 4A:
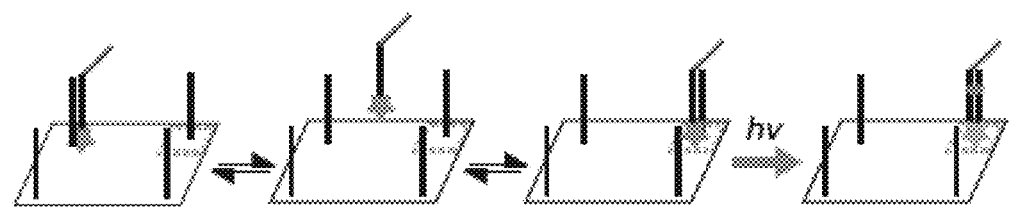
FIGS. 4A-C illustrate (A) the Action-PAINT mechanism, (B) the photo-crosslinking mechanism, and (C) CNVK photo-crosslinking bulk experiment.

DNA-PAINT is coupled with a photochemical process to permanently immobilize the transiently bound imager strand to achieve programmable and site-specific labeling with nano-scale precision. One simple implementation of this scheme (FIG. 4A) involves first attaching a conjugation handle (e.g. a biotin or another single-stranded DNA domain) and a photo crosslinker to the imager strand, and then triggering a fast photo-cross linking reaction between the imager and the docking strands when the imager strand binds to a docking strand on a target in the region of interest. The target in this location is thus linked to the conjugation handle and can be further manipulated or analyzed. When the docking strand lands outside the region of interest, cross-linking is not triggered.

Super-resolution DNA Probe Capture on a Synthetic DNA Nanostructure Platform.

Figure 4B:
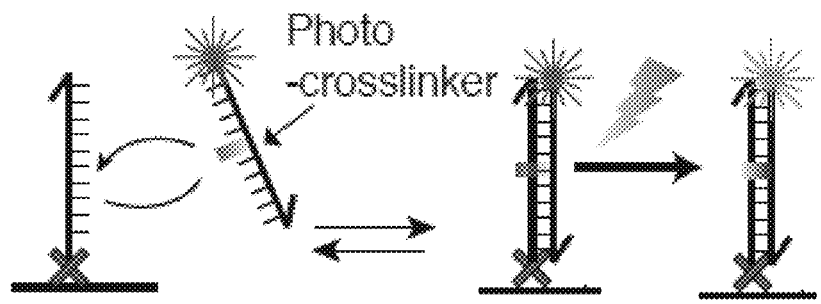
Figure 4C:
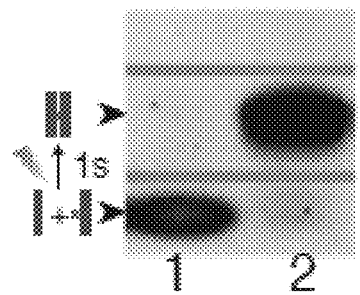

The photo-reactive nucleobase analog 3-cyanovinylcarbazole ($^{CNV}K$)[4,45] can be used as the photo-crosslinker (FIG. 4B). In a DNA duplex containing $^{CNV}K$, UV light (350-405 nm) can induce the fast cross-linking between the $^{CNV}K$ and the thymine (T) or cytosine (C) on the opposite strand, thereby forming a covalent link between the two strands. When the intensity of the irradiation is sufficiently high the photo cross-linking can proceed to completion within a second. As shown in FIG. 4C, efficient cross-linking (>90%) between a 10-nt oligo and a $^{CNV}K$ containing complementary oligo was achieved within 1 second of 365 nm light exposure.

The system can be benchmarked using a rectangular DNA origami nanostructure, which served as a calibration standard in previous super-resolution imaging methods.[32] The experiment may be performed as described below.

Figure 5:
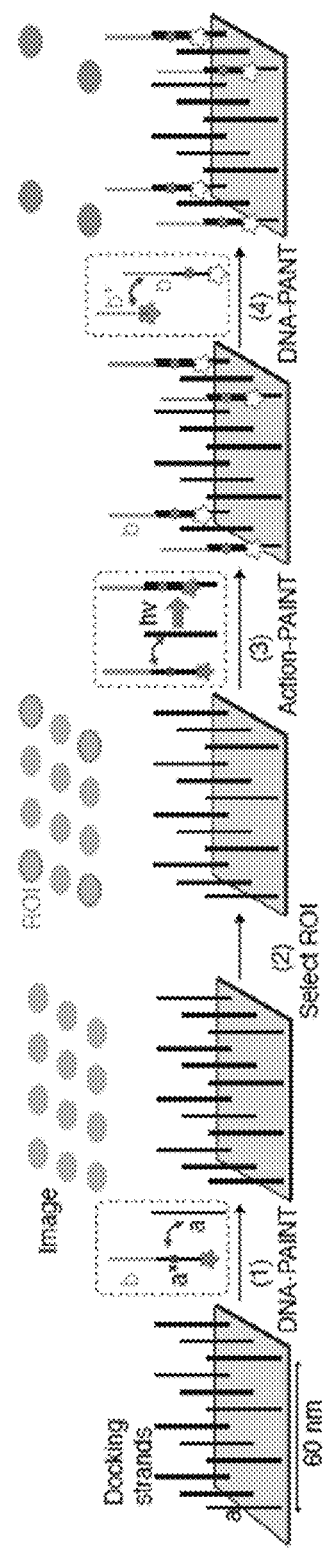
FIG. 5 illustrates benchmarking Action-PAINT using a rectangular DNA origami structure.
Figure 6A:
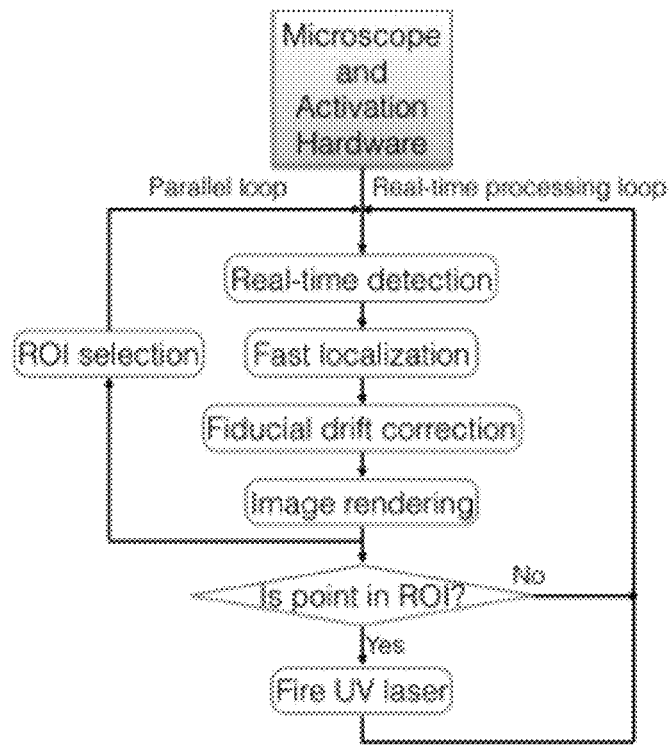
FIGS. 6A and B illustrate (A) Action-PAINT automated acquisition, processing, and actuation software, and (B) Activation laser spatial control by DMD array.
Figure 6B:
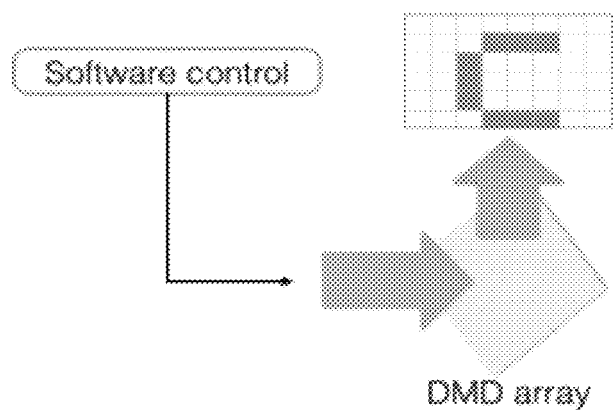

The rectangular DNA origami nanostructure displays 12 docking strands in a 3-by-4 20 nm grid. To demonstrate super-resolved labeling, the $^{CNV}K$-containing imager strand is covalently labeled to only the docking strands at the 4 corners. Specifically, all docking strands contain the same 9-nt sequence α, while the fluorescently labeled imager strand contains two domains: sequence "a*" (essentially complementary to "a" but contains a $^{CNV}K$ modification) and sequence "b". For the initial characterization only one DNA origami nanostructure is analyzed per field of view. As schematically illustrated in FIG. 5, the experiment contains 4 phases. (1) In the localization phase, binding of the imager strand to the docking strands on the DNA origami nanostructure are monitored using standard DNA-PAINT. After ~10 min of imaging, the positions of all 12 docking strands on the DNA origami nanostructure can be determined and stored. (2) In the ROI selection phase, the user specifies the docking sites (i.e., in ROI, region of interest) to be modified in the next step (indicated as circle). (3) In the labeling phase, whenever an imager strand binds a docking strand on the studied DNA origami nanostructure, its localization will be quickly determined by a real-time software program to decide whether it is on the corner. If it is, then the software will trigger the firing of the UV source to induce the cross-linking between the imager strand and the docking strand. Next, a strong laser pulse will be delivered to bleach the fluorophore on the cross-linked imager strand. This process will be repeated until all 4 corners are labeled with an imager strand. (4) In the analysis phase, the initial imager strand is washed away and a secondary imager strand, with sequence "b*" is added. The second imager strand will be used in standard DNA-PAINT to visualize the location of the cross-linked initial imager strand. Only the 4 corners of the DNA origami nanostructure as expected to 'light up'.

Software. The method will typically be performed using software that allows real-time detection, localization, selection, and cross-linking of the imager strand. Suitable software fulfills two requirements. The first requirement is real-time detection and processing of the DNA-PAINT super-resolution image. Transient DNA-PAINT binding events are to be detected and localized during the localization phase. Any stage drift over time is corrected as part of this processing routine to ensure high-resolution imaging and targeting. The second requirement is real-time selection and feedback based on the above information. This is required to ensure cross-linking of the imager strand during the short time frame it is bound to its respective docking strand. The transient nature of the binding events requires the whole process to be smoothly integrated and performed in real time. The delay introduced by the software computational cycle should be minimized to be shorter than the duration of an average binding event (0.5-2 seconds) to ensure successful cross-linking.

Algorithms capable of fast and accurate detection and localization that achieve minimum localization error are known.[46] Such algorithms provide theoretically best fitting accuracy compatible with demanding super-resolution needs, and also efficiently use GPU computing to accelerate the processing rates to allow real-time imaging processing. Drift correction will be based on tracking of drift markers made of gold nanoparticles and specially designed nucleic acid nanostructures. The combination of both approaches allows for fast and accurate drift correction, enabling highly demanding super-resolution imaging. Real-time reporting could also be implemented in the cases where newly activated targets are monitored in real-time in a spectrally separate channel. The processed localizations can then be pooled and rendered into a super-resolved image for an end user to view and analyze in real-time and make decisions of target selection for the latter activation step. The software will also include a custom Region Of Interest (ROI) selection from the rendered image.

Hardware. To provide real-time site-specific activation of designated binding oligonucleotides, a UV laser with fast switching and illumination area control is used. The laser switch can be implemented with the acousto-optic tunable filters (AOTF) shutter with <30 ms switching delay. Laser illumination can be implemented with uncontrolled full-plane illumination. This approach is effective in producing local (<5 µm) site-specific labeling or perturbation with a desired pattern. As an example, a Nikon Ti microscope system equipped with a AOTF shutter with sub 30 ms switching may be used. Successful attempts have been previously reported for integration with Nikon microscope system.[8]

To achieve more efficient large-field site-specific patterning, a Digital Micromirror Device (DMD) array is used to achieve parallel switching of UV laser illumination over the whole field, as described above. Such a DMD array device provides a large pixel array for partitioning of the whole illumination field; custom control is possible over each pixel, allowing each pixel to be switched either ON or OFF. This allows each microarray pixel to be controlled independently, while achieving similarly efficient manipulation and perturbation over a larger area. As an example, an Andor MOSAIC digital switching platform can be used as it provides pixel-based custom control over a large 1 M pixel array, and affords sub-ms switching delay.

Figure 7:
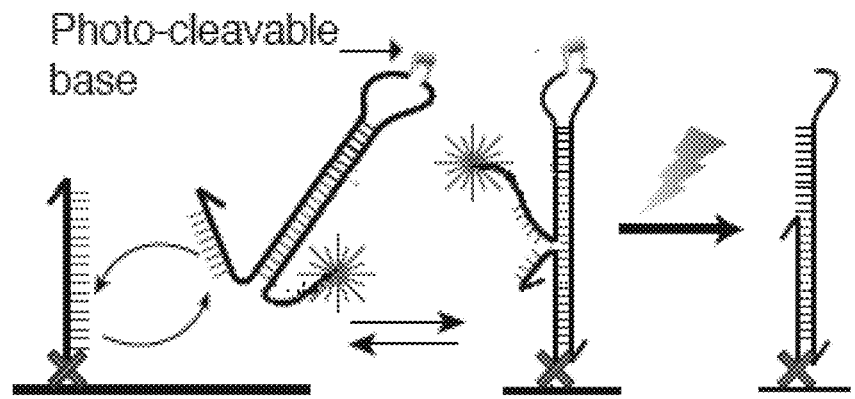
FIG. 7 illustrates photo-cleavage.

Alternative Immobilization Chemistry. The photo-cleavable linker o-nitrobenzyl and many of its derivatives have been shown to have excellent compatibility with biological systems due to minimum toxicity from the reactant and product. These compounds have been used in a wide variety of biological applications.[47,17,48] Some variants of the linker can even be cleaved with high-intensity visible light via two-photon effects,[49] thus eliminating the potentially mutagenic UV irradiation. A scheme has been developed to achieve photo-induced immobilization of imager strands by using a photo-cleavable linker rather than a photo cross-linker (FIG. 7). Here the imager strand assumes a hairpin structure and contains a photo-cleavable site in the loop. When the stem-loop is intact, the imager strand can only transiently interact with the docking strand via the short (~8-nt) toehold binding (FIG. 7), followed by the isoenergetic strand-displacement. When the photo-cleavable linker in the loop is cleaved, the strand-displacement can lead to an irreversible dissociation of one arm of the hairpin. Although in the final product the imager strand is not covalently linked to the docking strand, it is nonetheless stably hybridized to the docking strand.

Kinetics. DNA oligo binding times can be flexibly tuned in a wide range (0.1-10 s), with typical values around 0.5-2 s. Current imaging rates are typically at 100 ms per frame. Estimation based on current software processing speed shows efficient fitting and processing could be achieved within 100 ms, and hardware communication and activation within 30 ms. With 1 W/cm$^2$ UV laser power, the cross linking takes less than 1 s to finish. Added together, this guarantees that chemical activation will start within a delay of <300 ms after the binding event takes place; therefore for oligos with binding times around 2 s, this provides sufficient time (>1 s) for the cross-linking to occur.

Specificity. Specificity of modification is guaranteed by ensuring binding events are temporally separated from each other, so that erroneous activation does not occur because of two consecutive bindings. Specificity can be achieved as follows. DNA-PAINT binding bright time (ON-time) and dark time (OFF-time) can both be tuned independently and with a wide dynamic range. The binding ON/OFF time ratio can be tuned to be low enough such that, in each diffraction-limited area, the probability of blinking is low (<1/10). This guarantees >90% correctness in activation. In the event erroneous detection and activation has occurred, we could take advantage of the reversibility of the photo-crosslinking chemistry, and use similar methods for detaching the oligos under 312 nm UV illumination.[4]

Action-PAINT in 3D

Figure 8A:
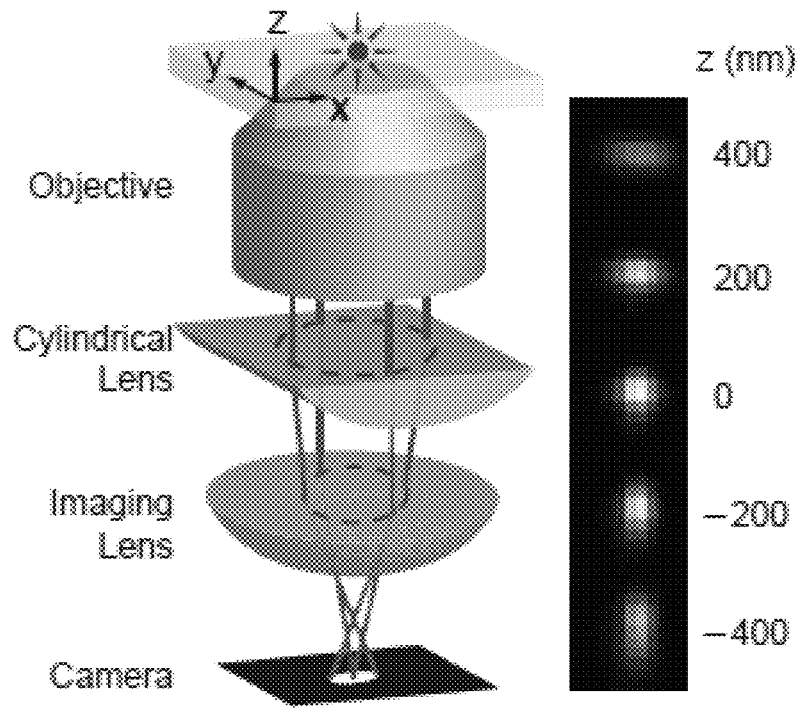
FIGS. 8A-C illustrate 3D DNA-PAINT super-resolution imaging hardware[39,22].

Two Action-PAINT implementations in three dimensions are proposed. One is suited for applications close to a surface, and the other is applicable for deeper 3D penetration such as whole cell or even tissue applications. For applications of Action-PAINT close to the cover glass surface, astigmatism-based 3D super-resolution imaging in combination with highly inclined and laminated optical sheet (HILO)[44] illumination will be used. This allows sub-diffraction detection and subsequent Action-PAINT modification for ~1 µm depth-of-field applications. In astigmatism-based single-molecule imaging, a cylindrical lens used in the imaging path "converts" the spherical point spread function (PSF) of a molecule to an elliptical PSF when imaged out of focus (FIG. 8A).

Figure 8B:
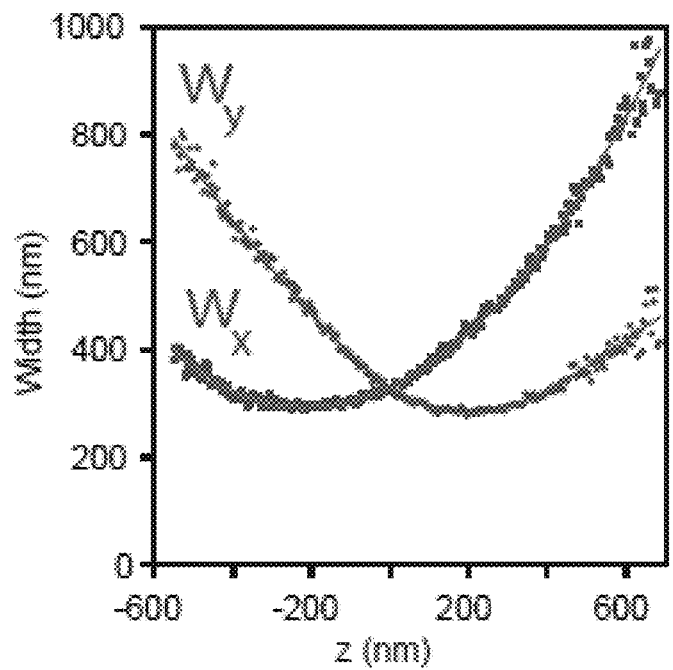
Figure 8C:
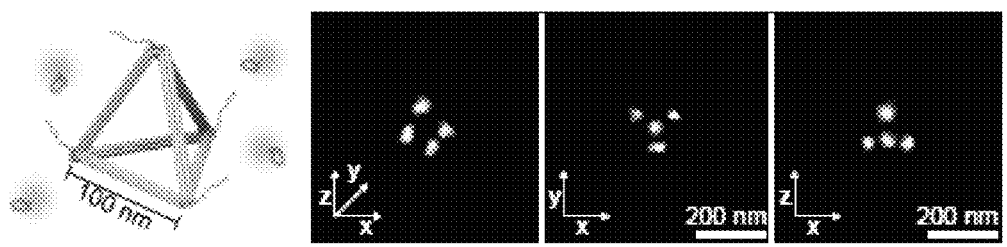

The degree and orientation of the elliptical PSF depends on the displacement and direction of the point source from the current focal imaging plane and is used to determine its z position with sub-diffraction accuracy (FIG. 8B). The implementation of astigmatism-based 3D Action-PAINT is as follows: since the detection and actuation (i.e., the immobilization of a DNA strand using a UV pulse for crosslinking) relies on the fact that only a single probe binds and is detected in a diffraction-limited voxel (a prerequisite for single-molecule-based 3D super-resolution microscopy), a 3D DNA-PAINT technique[32,39] can be used to localize molecules in this voxel (~200×200×1000 nm) with currently ~5 nm accuracy in x, y and ~10 nm in z, determine if binding occurs in a specified 5×5×10 nm voxel, and if binding is occurring immobilize the probe with high accuracy in 3D. Sub-diffraction-sized 3D DNA polyhedral structures can be used as a control in which all vertices of the structures carry the same DNA-PAINT docking site (FIG. 8C). After surface immobilization, a 3D DNA-PAINT image is acquired. The top point of the tetrahedron can be defined for Action-PAINT modification. The software described herein can be readily extended for real-time 3D detection and actuation.

For deeper 3D imaging, TIRF or HILO illumination are less suitable for 3D DNA-PAINT (and thus Action-PAINT) due to the increased out-of-plane fluorescence from freely diffusing imager strands that deteriorates the high signal-to-noise detection ratio necessary for efficient localization of single molecules. To overcome this limitation, a spinning disk confocal laser microscope is used for deep penetration 3D Action-PAINT, allowing us to obtain sub-diffraction site-specific 3D labeling over several tens of micrometers (i.e., throughout whole cells and potentially tissues or small organisms). For the imaging of structures far above the cover glass surface, confocal microscopy has been widely used, because its optical sectioning capability affords images with good signal-to-noise ratio. Recently, spinning disk systems were used for single-molecule super-resolution imaging when using spontaneously blinking fluorescent molecules.[50] Given the fact that DNA-PAINT probes autonomously blink (without the need for photoswitching), the 3D sectioning capability of a spinning disk confocal should be applicable to the methods provided herein. Practically speaking, deep-penetration 3D Action-PAINT imaging and labeling can be performed using a spinning disk confocal microscope in a ~1 µm thick z-slice at a time. Sub-diffraction super-resolution capability will be obtained by optical astigmatism imaging as described above.

Action-PAINT in Cells

Two concurrent cellular studies are performed. In the first study, a nanoscale DNA probe is attached to a DNA origami nanostructure anchored to the surface of a fixed cell or microinjected into the cells and present either in the cytoplasm or the nucleus. In the second study, Action-PAINT is used to directly label protein targets in the fixed cell (e.g., labeling a microtubule network at a periodical interval of 20 nm).

DNA-PAINT Cellular Imaging. Super-resolution imaging of cellular structures using DNA-PAINT has been demonstrated.[32] Furthermore the cytoskeleton microtubule network in a fixed HeLa cell has been imaged (FIG. 8a) using DNA-conjugated antibodies. In addition, optical astigmatism[22,51] was used to obtain 3D super-resolution images of a microtubule network inside a fixed HeLa cell (FIG. 9B; where color is indicated height).

Action-PAINT on DNA Structures Attached to Cell Surface or Microinjected into a Cell. To evaluate the performance of Action-PAINT in the context of cellular environment, a high-precision DNA oligo modification to a single specified point on a DNA tetrahedron attached to the cellular surface is performed. Anchoring the DNA nanostructures to cell surface is achieved via immunolabeling of over-expressed surface receptors (such as EGFR) using pre-assembled antibody DNA origami conjugates (FIG. 9C). After cellular anchoring, the four corners of the tetrahedron structure are resolved using super-resolution DNA-PAINT imaging. Here, similar to the previous in vitro experiment, the DNA-PAINT imaging is performed using fluorescently labeled imager strands containing two sequence domains. The first domain is a sequence complementary to the docking strand on the tetrahedron structure and contains a $^{CNV}$K modification. The second domain is a unique conjugation handle, which is available after Action-PAINT nanoscale modification of the tetrahedron structure, for performance characterization through a second round of DNA-PAINT. Next, software and hardware components as described herein, 3D-Action-PAINT is performed to specifically attach an imager strand to a single, specified vertex of the 3D nanostructure. The performance of the nanostructure modification on the cell surface is evaluated using a second round of DNA-PAINT. This experiment yields information regarding the parameters that affect cellular performance.

The next experiment is performed to demonstrate the ability to modify nanostructures inside fixed cells (FIG. 9D). DNA tetrahedral nanostructures are microinjected into the nucleus and cytoplasm of fixed cells. The nanostructures are visualized using DNA-PAINT, and particular vertices are modified using Action-PAINT. This experiment facilitates calibration and mitigation of deviations (if any) from the reference results obtained from cell surface.

Figure 9E:
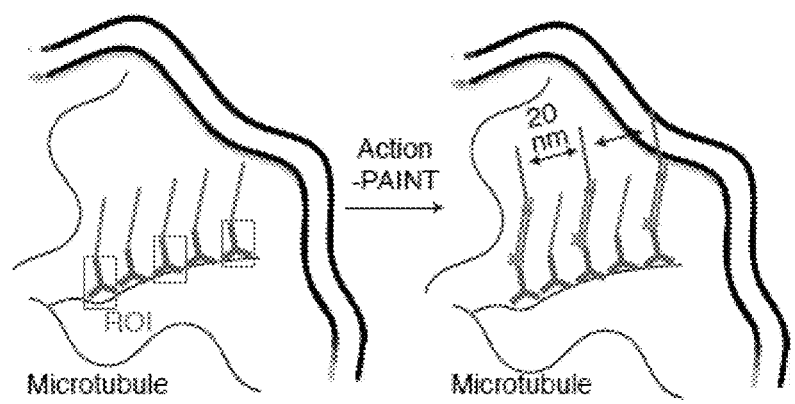

Action-PAINT to Label Cellular Protein Structures. In a further experiment, Action-PAINT is used to achieve site-specific labeling of proteins in the fixed cells. In one experiment, a microtubule network is periodically labelled. DNA strands are anchored on the entire microtubule network by using microtubule targeted antibody conjugate bearing a DNA strand. After acquiring a DNA-PAINT image of the microtubule network, Action-PAINT is performed to permanently immobilize DNA probes in a user-specified pattern, e.g., at periodic 20 nm intervals (FIG. 9E). Thereafter, the patterned microtubule structure is imaged by DNA-PAINT to evaluate the performance of the protein modification. These cellular experiments allow further optimization of certain parameters involved in cellular Action-PAINT, including the choice of imager sequence having low non-specific binding, the laser power, and the time needed for optimal cross-linking. In still another experiment, DNA-PAINT is used to label cell surface protein clusters with periodic patterns (e.g., 20 nm grid).

In some instances, full scale antibodies are replaced with nanobodies, particularly where high-density imaging is desired. In some instances, the imager and docking strands are designed such that a T or C is present at the −1 position in the docking strand DNA in the $^{CNV}$K cross-linking implementation. This is expected to minimize non-specific cross-linking. Additionally, to eliminate sequence similarity that could result in undesired cross-linking of the $^{CNV}$K-containing imager strand with the cell's own nucleic acids, $^{CNV}$K-containing imager strand sequence will be screened against the genomic content of the cell.

Applications

The methods provided herein may be used to analyze protein specific interactions at a single cell level. Compared to previous approaches that use engineered genetic tags of small molecule reagents confined to genetically accessible, cellular compartments (e.g. APEX),[34-36] the approach provided herein with real-time optical feedback allows for an arbitrary labeling and perturbation pattern, with the potential of incorporating an end user's decision based on information from the real-time super-resolution imaging data. Furthermore, this new approach can be performed on a single cell level, providing end users with unprecedented knowledge of cell-specific proteomics information and stochastic fluctuation of cellular behavior.

The methods provided herein may also be used in nanoscale optogenetics including in spatiotemporally controlled single ion channel manipulation. Previous approaches in investigating ion channel effects on neuron firing and activity levels have been limited to batch-based switching only, due to a lack of manipulation tools that can both detect and perturb the ion channel behavior with a super-resolution precision. Using molecular perturbing agents such as lumitoxin,[37] the approach provided herein offers an integrated toolset that allows super-resolution and molecule-specific visualization and manipulation of these ion channels. This will facilitate the identification and delineation of the effects of each single ion channel in a dense cluster and enable further study of the effect of their clustering arrangement.

These applications will be described in more detail below.

Action-PAINT to Enable Nanoscale Single-cell Spatial Proteomics

This example describes a first method for nanoscale single-cell spatial proteomics. The method specifically captures and identifies a particular protein and its associated partners at a user-specified location in the cell. The ability to specifically capture and identify particular protein targets and their associated partners enables a detailed understanding of protein network architecture from single cells in a site-specific fashion.

Delineating protein interaction networks in cells has been traditionally addressed using mass spectrometry (MS)-based proteomics, which is limited to cellular compartments that can be isolated in high yield and purity. However, many cellular protein interactions are difficult to purify, and as a result the "interactome" of certain proteins cannot be explore using prior art methods. A more recent technique enables mapping of specific protein interactomes in living cells using an engineered ascorbate peroxidase (APEX).[34-36] However, APEX-based protein network mapping is obtained from averaging protein interactions from a large population of cells rather than from a single cell. Further, it has also been hypothesized that certain proteins have completely different interacting protein partners, depending on their cellular function and these interactions cannot be mapped using APEX-based biochemical characterization. Importantly, methods for location-specific labeling based on genetic tags (such as APEX) are restricted to genetically accessible locations, and cannot achieve arbitrary user-specified location selection. In contrast, Action-PAINT enables the user to "grab" a protein at an arbitrary user-specified location.

Figure 3F:
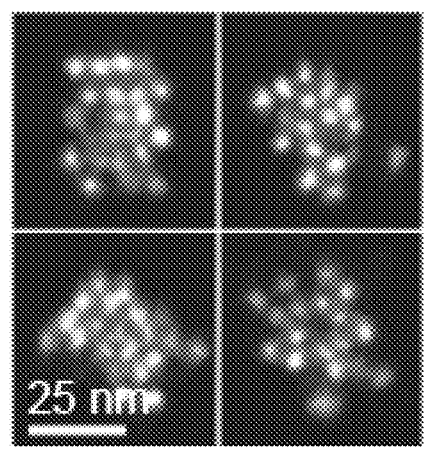
Figure 10A:
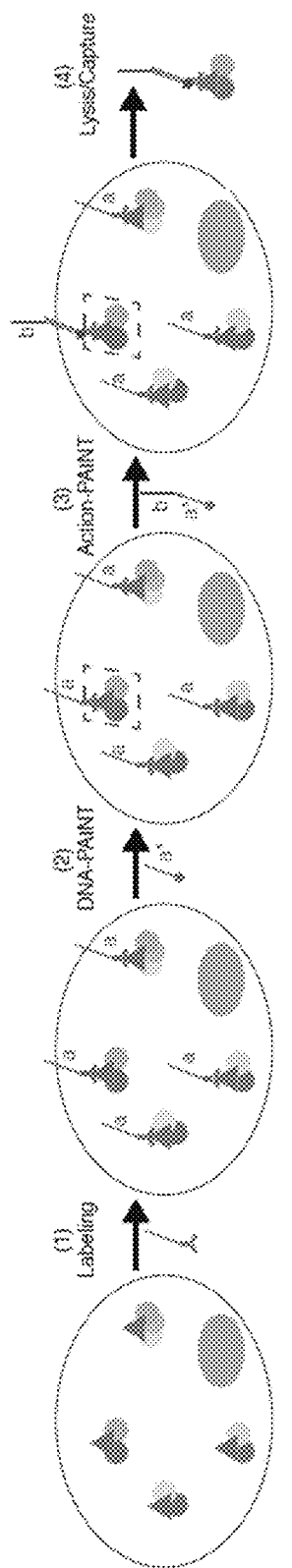
FIGS. 10A-B illustrate nanoscale single-cell spatial proteomics.

Nanoscale Spatial Labeling and Capturing. FIG. 10A provides the design of these methods. In step 1, the cells are fixed and the target protein is labeled with antibodies conjugated to docking strands (sequence a). In step 2, DNA-PAINT super-resolution imaging is performed with resolution of ~5 nm (FIG. 3F). This allows the spatial identification of the location of target protein with sub-diffraction resolution. In step 3, using Action-PAINT the docking strand in ROI (box) will be modified using an imager strand that carries a conjugation handle (sequence b). In step 4, the cell is lysed and the contents are captured in an imaging chamber using a complementary strand (b*) to the conjugation handle b, which allows the isolation of the protein complex of interest. The proteins in the complex are then identified using a single protein optical finger-printing method as described below. The proceeding experiment can be carried out in both 2D and 3D.

Figure 10B:
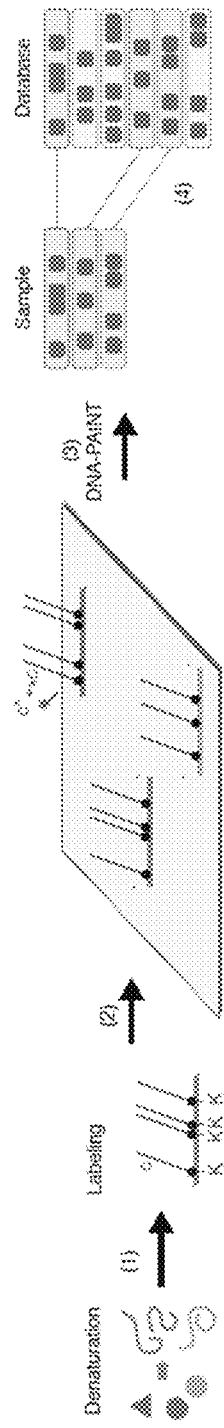

Single Protein Identification Via Super-Resolution Fingerprinting. "Protein-fingerprinting" is achieved by attaching DNA (modified with chemical tags) to specific amino acid residues (e.g. lysines with NHS-ester chemistry) and imaging with DNA-PAINT ultra-high resolution (2 nm localization accuracy). FIG. 10B provides the design of these methods. In step 1, the protein complexes captured from the previous method (above) are denatured and stretched using chemical agents such as SDS. All lysine residues in the peptide chain are specifically labelled with another tag, which comprises a DNA-PAINT handle and in this instance a click chemistry reacting group (such as TCO). Other conjugation means can be used in place of the click chemistry reacting group. In step 2, the stretched peptide chains with attached click chemistry anchors are fixed on a surface fully decorated with the counter-acting click chemistry group (such as TZ). In step 3, ultra-high resolution DNA-PAINT imaging with the newly labelled DNA-PAINT handles is used to display the positions of all the lysine residues, with <2 nm localization accuracy. The collection of all identified lysine residues in a stretched peptide chain provides a barcode-like representation of the lysine distribution in the peptide sequence. The combinatorial diversity of specifically-labelled residues allows for unique identification of proteins (library size >$10^7$). In step 4, this barcode information is compared and matched to the library of all genetically identified protein coding sequences from whole genome sequencing, and the identity of the current protein is then determined.

With this approach, proteins from the same protein complex will be close to each other, and can be separated from those from a different complex. Each single component within a large protein complex can also be identified, and directly matched to its genetic sequence, without the need of any prior knowledge of the protein component and without the use of a pre-existing antibody against each component. Multiple rounds of residue-specific barcode imaging may be performed with Exchange-PAINT,[32] in order to further identify proteins with similar barcodes, or to study special features such as phosphorylation and post-translational modification patterns.

Application to Motor Proteins. Previous work has determined that motor proteins such as myosin, kinesin and dynein have completely different protein interaction network depending on the cellular cargo with which they are associated[52,53] or their location within the cellular environment (e.g., even when associated with the same cargo).[54] Most of the existing protein interaction mapping studies for these motor proteins come from bulk biochemistry and some single molecule analysis data.[55-57] Using the techniques described herein, unique DNA handles can be attached to protein targets to facilitate pull-down and protein profiling of individual motor protein complexes present in different cellular locations within a single cell. One suitable complex is the protein interactome of kinesin-1 motor proteins since it is widely studied using other previous systems and the results can be compared to those previously obtained as validation.[58]

First, mammalian cells are fixed and DNA anchor oligos are attached to kinesin-1 motor protein via pre-assembled kinesin-1 antibody-DNA conjugates.[32] Then DNA-PAINT super resolution imaging is performed to map the cellular location of all kinesin-1 motor proteins within a cell. Further, the experiment can be used to study the interaction of the kinesin-1 interactome with different forms of cellular cargo (e.g., mRNA, lipids, mitochondria, etc.). This can be accomplished by performing multiplexed DNA-PAINT imaging and choosing only those kinesin-1 proteins that co-localize with a particular cargo type and are present on microtubules, the latter feature indicating a kinesin-1 that is in the process of active cellular transport. Then, as described previously, using DNA modified with a photo-crosslinking or photo-cleaving DNA base, a unique DNA handle is attached to specific kinesin-1 protein complexes of interest and its protein interactome can be examined by following the process outlined above. By understanding the variation of in a kinesin-1 interactome for the same cargo in different cellular locations or for different cargo in the same cellular location, it will be possible to understand the particular biological function of certain kinesin-1 adaptor proteins such as JIP1, Miro, Milton, FMRP, etc.[59] Similar techniques can be used for other members of the kinesin superfamily or other molecular motors (such as myosin and dynein).

DNA-PAINT handles are labelled on each of the lysine residues of a stretched peptide chain. Lysine specific modification can be achieved with NHS ester chemistry. In some instances, particularly where potential crowdedness is a concern, a long linker can be included between the NHS group and the DNA-PAINT handles. Recent data show that a linker of about 10 nm in length does not sacrifice the localization accuracy (data not shown).

Estimation of the possible library size encoded by the variable positioning of lysine residues may be performed as follows. Assume a typical protein coding peptide chain has 300 residues. The imaging capability described herein allows positioning down to 2 nm accuracy (data not shown), which is equal to ~10 peptide bonds. Dividing the whole peptide chain into 10 peptide bond sections (300/10) results in about 30 sections. Each section is assigned 1 if a lysine is present or 0 if no lysine is present. Such 0 or 1 assignments, yields $2^{30}$ (or $10^9$) different possibilities. In practice, however, lysine distribution in the protein coding sequence is about 7%, which means on average there will be 21 lysine residues within a protein, this gives $(30,21)=1.4 \times 10^7$ possibilities. The current estimated number of genes in the human genome is below 100,000, which is well below the library size allowed here.

In the event two proteins have a similar or identical lysine signature, an additional screening can be performed with a different residue-specific chemistry, such as for example cysteine or arginine, via Exchange-PAINT.[32] To image multiple rounds of different amino acid signatures, a photo-cleavable linker is placed before the DNA-PAINT oligo, so that after imaging, the label oligo can be removed by UV light illumination. This allows chemical modification of a second amino acid, given the tight space that is allowed on the peptide strand.

An incompletely stretched peptide sequence can potentially provide an erroneous signature (such as a missing segment in the middle of a chain) and may result in incorrect protein identity assignment. To address this issue, amino acid signatures can be matched first locally and then assembled globally. This method is both computationally more effective (compared to whole sequence matching), and it provides more error tolerance of mis-stretched sequences.

The entire Action-PAINT and protein barcoding platform can be realized in an integrated microfluidics device. This disclosure contemplates an integrated flow platform providing adequate support for protein barcoding analysis.

Action-PAINT to Enable Nanoscale Optogenetics

Optogenetic tools have proven to be of great utility in neuroscience. These analysis techniques cause voltage changes in cells through delivery of exogenous ion channels, followed by illumination, and ion translocation.[60] As a result, they cannot be used to analyze the impact of endogenous ion channels on neural computation. Meanwhile, there is growing appreciation that the precise identity and distribution of endogenous ion channels is important for neural computation. For example, dendritic potassium channels can precisely sculpt the propagation of neural activity into different compartments of neurons, and in epilepsy, this excitability control may be corrupted, causing hyperexcitability.[61] In certain subsets of neurons, like at the axon hillock, the action of a relatively small number of sodium channels can control whether a neuron generates and broadcasts an action potential.[62] Thus, the ability to control small sets of ion channels may be of great utility in the study of how neurons integrate neural inputs from upstream neurons to generate spikes that then are transmitted to downstream neurons. Even the drive or blockade of an individual or a set of individual ion channels may be of great utility. Indeed, a theoretical study has indicated that discrete channel noise, due to the flickering influence of single ion channels, may be critical for slow peri-threshold oscillations in certain stellate neurons of the entorhinal cortex.[63] Models that do not take into account the stochastic gating of individual ion channels exhibit more impoverished neural dynamics than models that do.[64] Another theoretical study has implied that the ability of a neuron to encode inputs into spikes can be optimized by ion channel noise, if the ion channels operate in clusters of a certain size, or if ion channels are considered as discrete entities that probabilistically flicker open or closed, in contrast to being considered only as coordinated populations with aggregate dynamics.[65] No previous technology allows for the blockade or drive of an individual ion channel with temporal precision, and thus models of how the stochastic nature of ion channel gating might contribute to neural dynamics remain unexplored. Experimental investigation has been confined to a small subset of channels such as calcium channels, where imaging of nanodomains has become possible, indicating that near the ion channel power, massive concentrations of calcium can occur transiently,[66] and channel clustering can enhance this process.[67] Indeed, calcium channels may compete for sparse "slots" at synaptic connections, meaning that the identity of specific calcium channels may be important at the individual level.[68] However, beyond this specific case of calcium channels, no generalized way to investigate individual channels or small clusters has become apparent.

This disclosure contemplates the use of Action-PAINT to enable, for the first time, nanoscale optogenetics (i.e., the ability to precisely control the activity of individual ion channel at a user-specified location with nanometer precision). Nanoscale optogenetics will allow the perturbation and analysis of neuronal function with much better precision and will help to broadly enable true molecular, rather than cellular, understanding of neuronal function.

Ion channels and receptors in the cell membranes and internal membranes are often distributed in discrete clusters with an average diameter of 100 nm.[69] These clusters are randomly distributed throughout the cell membrane and each of these clusters are known to contain a few to hundreds individual ion channels.[67] Hence in order to delineate the contribution of single ion channels, techniques are needed that are capable of activating or deactivating individual ion channels in a temporally precise and reversible manner with nanometer precision.

Recently, a novel protein architecture (lumitoxin) was developed by that is capable of modulating endogenous ion channels by being fully genetically encoded and activated by light.[37] Lumitoxin is a fusion protein comprising two functional elements, peptide neurotoxins and the photoreceptor LOV2-J, and which serves as the tether between the protein ligand of interest and the membrane. Using lumitoxin and blue (455 nm) light on PC12 cell and Kv channels, it was shown that the majority of ion channels were deactivated in the dark state and were activated within seconds of exposure to blue light. Whole-cell patch clamp recordings were used to determine the activity of the ion channels. Lumitoxin in combination with blue light is capable of controlling discrete ion channel clusters but is not capable of modulating a single ion channel since the diffraction barrier (~200 nm) cannot be broken with the blue laser source.

Figure 11A:
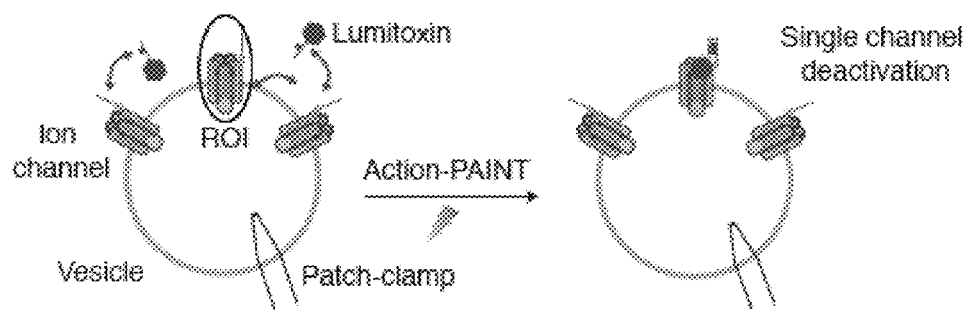
FIGS. 11A-C illustrates single ion channel manipulation.

In this disclosure, lumitoxin is used to control the activity of individual ion channels first in vitro, and then in living mammalian cells. Previous work has shown successful purification and reconstitution of active ion channels (TREK-1 and TRPV3) in liposomes and measurement of activity using patch-clamp recording.[47] The experiments for nanoscale single ion-channel manipulation will be performed in a synthetic liposome system (FIG. 11A). Specifically, these ion channel are first purified as described previously along with protein tags (such as SNAP) and a DNA anchor oligo (via O6-Benzylguanine) is attached to individual ion channels. As a next step, the purified protein with DNA oligo are reconstituted in lipids droplets and DNA-PAINT super-resolution imaging is used to understand the exact location and copy number of ion channels per proteoliposome.[32] Then, using Action-PAINT, DNA oligo coupled to lumitoxin is placed on individual ion channel of interest. Patch-clamp measurements before and after selective silencing or measuring activity of individual ion channel (using techniques such as single-molecule patch-clamp FRET microscopy[71]) are used to analyze the activity of individual ion channels.

Figure 11B:
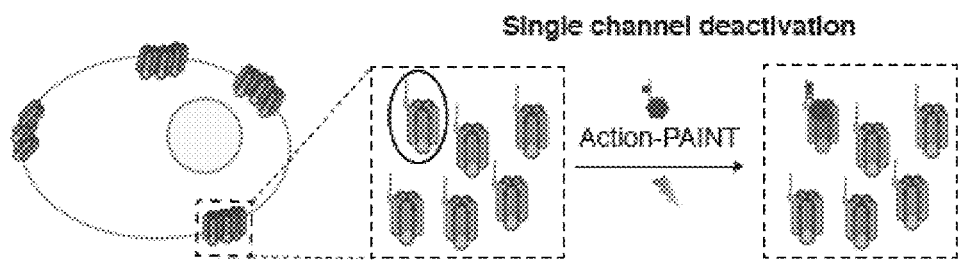

The contribution of single ion channel within a cluster in living cells may also be analyzed. In one experiment, a user-specified channel may be deactivated using Action-PAINT to deliver to it a lumitoxin cargo (FIG. 11B). First, the precise location of single ion channels within a cluster is determined using DNA-PAINT based super-resolution imaging (resolution ~5 nm). Then, using existing patch-clamp recording or single-molecule patch-clamp FRET microscopy the activity of the entire ion channel cluster is recorded.[71-73] Following this, a single ion channel of interest is identified, and a DNA oligo coupled to lumitoxin is placed near that ion channel using Action-PAINT to deactivate that channel. The next steps involve recording the activity of the ion channel cluster (while deactivating the targeted ion channel with blue light) and comparing such activity with previous recordings.

Figure 11C:
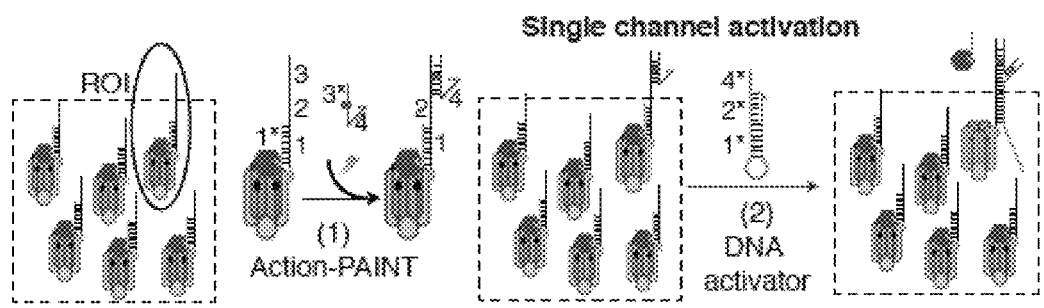

A complementary approach is to actuate a single user-specified ion channel (FIG. 11C). First, using cells in which the ion channels of interest is expressed with a protein tag a DNA docking strand is attached to such ion channels (similar as in FIG. 11B). Then, DNA-lumitoxin is attached to the handle such that every ion channel has a protein tag pair. Upon coupling to DNA-lumitoxin, the channel is rendered inactive unless activated with blue light. Now, by adopting a scheme as described in FIG. 11C, lumitoxin can be selectively removed from a single ion channel and the activity of the cluster measured to determine the contribution of a single ion channel. Specifically, in step 1, Action-PAINT is used to conjugate the (3*-4*) strand to the strand which is linked to the chosen ion-channel to be activated. In step 2, the activator hairpin is introduced; this will only specifically displace the DNA-lumitoxin from the ion-channel that is modified with the strand in step 1, through toehold-mediated strand displacement reaction initiated by the "toehold" segment 4. In this way, only this particular ion channel will be activated.

The nanoscale optogenetics tools described herein can be used for example to study the effect of nanoscale spatial modulation of ion channels for precise signal integration and propagation, as well as the subtle role of discrete ion channel noise.

REFERENCES

[1] Rust, M. J., Bates, M., Zhuang, X. Stochastic optical reconstruction microscopy (STORM) provides sub-diffraction-limit image resolution. *Nature Methods* 3(10), pp. 793-795 (2006).

[2] Sharonov, A., Hochstrasser, R. M. Wide-field subdiffraction imaging by accumulated binding of diffusing probes. *PNAS* 103(50), pp. 18911-18916 (2006).

[3] Jungmann, R., Steinhauer, C., Scheible, M., Kuzyk, A., Tinnefeld, P., Simmel, F. C. Single-molecule kinetics and super-resolution microscopy by fluorescence imaging of transient binding on DNA origami. *Nano Letters* 10, pp 4756-4761 (2010).

[4] Yoshimura, Y., Fujimoto, K. Ultrafast reversible photo-cross-linking reaction: toward in situ DNA manipulation. *Organic Letters* 10, pp. 3227-3230 (2008).

[5] Fujimoto, K., Konishi-Hiratsuka, K., Sakamoto, T., Yoshimura, Y. Site-specific photochemical RNA editing. *Chemical Communications* 46, pp. 7545-7547 (2010).

[6] Shigeno, A., Sakamoto, T., Yoshimura, Y., Fujimoto K. Quick regulation of mRNA functions by a few seconds of photoirradiation. *Organic & Biomolecular Chemistry* 10, pp. 7820-7825 (2012).

[7] Fujimo, K., Konishi-Hiratsuka, K., Sakamoto, T. Quick, Selective and reversible photocrosslinking Reaction between 5-methylcytosine and 3-cyanovinylcarbazole in DNA double strand. *International Journal of Molecular Sciences* 14(3), pp. 5765-5774 (2013).

[8] Levskaya, A., Weiner, O. D., Lim, W. A., Voigt, C. A. Spatiotemporal control of cell signalling using a light-switchable protein interaction. *Nature* 461, pp. 997-1001 (2009).

[10] Texas Instruments (TI) (Posted: August 2012, Rev. Sept. 2012). "DLP9500: DLP® 0.95 1080p 2×LVDS Type A DMD." Retrieved (Apr. 20, 2013) from: <http://www.ti.com/lit/ds/dlps025a/dlps025a.pdf>.

[11] Hinrichsen, E. L., Feder, J., Jøssang, T. Geometry of random sequential adsorption. *Journal of Statistical Physics* 44(516), pp. 793-827 (1986).

[12] Cadilhe, A., Araujo, N. A. M., Privman, V. Random sequential adsorption: from continuum to lattice and pre-patterned substrates. *Journal of Physics: Condensed Matter* 19, 065124 (2007).

[13] Torquato, S., Uche, O. U., Stillinger, F. H. Random sequential addition of hard spheres in high Euclidean dimensions. <arXiv:cond-mat/0608402>

[14] Andor Technology (Andor). "iXon EMCCD Camera Series." Retrieved (Nov. 23, 2013) from: <http://www.and/or.com/scientific-cameras/ixon-emccd-camera-series>.

[15] Hamamatsu Corporation. "Digital CMOS camera-ORCA-Flash 4.0 V2 C11440-22CU." Retrieved (Nov. 23, 2013) from: <http://www.hamamatsu.com/jp/en/community/life_science_camera/product/search/C11440-22CU/index.html>.

[16] Pertsinidis, A., Zhang, Y., Chu, S., Subnanometre single-molecule localization, registration and distance measurements. *Nature* 466, pp. 647-651 (2010).

[17] Piestun, R., Schechner, Y. Y., Shamir, J. Propagation-invariant wave fields with finite energy. *Journal of the Optical Society of America A* 17, pp. 294-303 (2000).

[18] Betzig, E., Patterson, G. H., Sougrat, R., Lindwasser, O. W., Olenych, S., Bonifacino, J. S., Davidson, M. W., Lippincott-Schwartz, J., Hess, H. F. Imaging intracellular fluorescent proteins at nanometer resolution. *Science* 313, pp. 1642-1645 (2006).

[19] Pavani, S. R. P., Thompson, M. A., Biteen, J. S., Lord, S. J., Liu, N., Twieg, R. K., Piestun, R., Moerner, W. E. Three-dimensional single-molecule fluorescence imaging beyond the diffraction limit using a double-helix point spread function. *PNAS* 106, pp. 2995-2999 (2009).

[20] Lee, H. D., Sahl, S. J., Lew, M. D., Moerner, W. E. The double-helix microscope super-resolves extended biological structures by localizing single blinking molecules in three dimensions with Nanoscale precision. *Applied Physics Letters* 100(15), 153701 (2012).

[21] Backlund, M. P., Lew, M. D., Backer, A. S., Sahl, S. J., Grover, G., Agrawal, A., Piestun, R., Moerner, W. E. Simultaneous, accurate measurement of the 3D position and orientation of single molecules. *PNAS* 109, pp. 19087-19092 (2012).

[22] Huang, B., Wang, W., Bates, M., Zhuang, X. Three-dimensional super-resolution by stochastic optical reconstruction microscopy. *Science* 319(5864), pp. 810-813 (2008).

[23] Ram, S., Chao, J., Prabhat, P., Ward, E. S., Ober, R. J. A novel approach to determining the three-dimensional location of microscopic objects with applications to 3D particle tracking. *Proc. SPIE* 6443 (2007).

[24] Juette, M. F., Gould, T. J., Lessard, M. D., Mlodzianoski, M. J., Nagpure, B. S., Bennett, B. T., Hess, S. T., Bewersdorf, J. Three-dimensional sub-100 nm resolution fluorescence microscopy of thick samples. *Nature Methods* 5(6), pp. 527-529 (2008).

[25] Pavani, S. R. P., Piestun, R. Three dimensional tracking of fluorescent microparticles using a photon-limited double-helix response system. *Optics Express* 16(26), pp. 22048-22057 (2008).

[26] Middendorff, C. V., Egner., A., Geisler, C., Hell, S. W., Schonle, A. Isotropic 3D nanoscopy based on single emitter switching. *Optics Express* 16(25), pp. 20774-20788 (2008).

[27] Badieirostami, M., Lew, M. D., Thompson, M. A., Moerner, W. E. Three-dimensional localization precision of the double-helix point spread function versus astigmatism and biplane. *Applied Physics Letters* 97, 161103 (2010).

[28] Szilard, L. On the decrease of entropy in a thermodynamic system by the intervention of intelligent beings. *Zeitschrift fur Physik* 53, pp. 840-856 (1929).

[29] Toyabe, S., Sagawa, T., Ueda, M., Muneyuki, E., Sano, M. Experimental demonstration of information-to-energy conversion and validation of the generalized Jarzynski equality. *Nature Physics* 6, pp. 988-992 (2010).

[30] Vaughan, J. C., Jia, S., Zhuang X. Ultrabright photoactivatable fluorophores created by reductive caging. *Nature Methods* 9, pp. 1181-1184 (2012).

[31] Olejnik, J., Sonar, S., Krzymañska-Olejnik, E., Rothschild, K. J. Photocleavable biotin derivatives: a versatile approach for the isolation of biomolecules. *PNAS* 92(16), pp. 7590-7594 (1995).

[32] Jungmann, R.; Avendano, M. S.; Woehrstein, J. B.; Dai, M.; Shih, W. M.; Yin, P. *Nat. Methods* 2014, 11, 313-318.

[33] Manfrinato, V. R.; Wen, J.; Zhang, L.; Yang, Y.; Hobbs, R. G.; Baker, B.; Su, D.; Zakharov, D.; Zaluzec, N. J.; Miller, D. J.; Stach, E. A.; Berggren, K. K. *Nano Lett.* 2014, 14, 4406-4412.

[34] Martell, J. D.; Deerinck, T. J.; Sancak, Y.; Poulos, T. L.; Mootha, V. K.; Sosinsky, G. E.; Ellisman, M. H.; Ting, A. Y. *Nat. Biotechnol.* 2012, 30, 1143-1148.

[35] Rhee, H. W.; Zou, P.; Udeshi, N. D.; Martell, J. D.; Mootha, V. K.; Carr, S. A.; Ting, A. Y. *Science* 2013, 339, 1328-1331.

[36] Hung, V.; Zou, P.; Rhee, H. W.; Udeshi, N. D.; Cracan, V.; Svinkina, T.; Carr, S. A.; Mootha, V. K.; Ting, A. Y. *Mol. Cell* 2014, 55, 332-341.

[37] Schmidt, D.; Tillberg, P. W.; Chen, F.; Boyden, E. S. *Nat Commun* 2014, 5, 3019.

[38] Grotjohann T, Testa I, Leutenegger M, Bock H, Urban N T, Lavoie-Cardinal F, Willig KI, Eggeling C, Jakobs S, Hell SW. *Nature.* 2011 Sep. 11; 478(7368):204-8.

[39] Iinuma, R.; Ke, Y.; Jungmann, R.; Schlichthaerle, T.; Woehrstein, J. B.; Yin, P. *Science* 2014, 344, 65-69.

[40] Hell, S. W. *Science* 2007, 316, 1153-1158.

[41] Hell, S. W. *Nat. Methods* 2009, 6, 24-32.

[42] Huang, B.; Babcock, H.; Zhuang, X. *Cell* 2010, 143, 1047-1058.

[43] Hell, S. W.; Wichmann, J. *Opt Lett* 1994, 19, 780-782.

[44] Tokunaga, M.; Imamoto, N.; Sakata-Sogawa, K. *Nat. Methods* 2008, 5, 159-161.

[45] Vieregg, J. R.; Nelson, H. M.; Stoltz, B. M.; Pierce, N. A. *J. Am. Chem. Soc.* 2013, 135, 9691-9699.

[46] Smith C S, Joseph N, Rieger B, Lidke K A. *Nature Methods* 2010, 7, 373-375.

[47] Ellis-Davies, G. C. *Nat. Methods* 2007, 4, 619-628.

[48] Agasti, S. S.; Kohler, R. H.; Liong, M.; Peterson, V. M.; Lee, H.; Weissleder, R. *Small* 2013, 9, 222-227.

[49] Lusic, H.; Uprety, R.; Deiters, A. *Org. Lett.* 2010, 12, 916-919.

[50] Uno, S. N.; Kamiya, M.; Yoshihara, T.; Sugawara, K.; Okabe, K.; Tarhan, M. C.; Fujita, H.; Funatsu, T.; Okada, Y.; Tobita, S.; Urano, Y. *Nat Chem* 2014, 6, 681-689.

[51] Kao, H. P.; Verkman, A. S. *Biophys. J.* 1994, 67, 1291-1300.

[52] Bullock, S. L. *Biochem. Soc. Trans.* 2011, 39, 1161-1165.

[53] van den Berg, R.; Hoogenraad, C. C. *Adv. Exp. Med. Biol.* 2012, 970, 173-196.

[54] Holt, C. E.; Bullock, S. L. *Science* 2009, 326, 1212-1216.

[55] Belyy, V.; Yildiz, A. *FEBS Lett.* 2014, 588, 3520-3525.

[56] Ishii, Y.; Ishijima, A.; Yanagida, T. *Trends Biotechnol.* 2001, 19, 211-216.

[57] De La Cruz, E. M.; Holzbaur, E. L. *J. Cell. Sci.* 2014, 127, 2997-2998.

[58] Vale, R. D. *Cell* 2003, 112, 467-480.

[59] Hirokawa, N.; Noda, Y.; Tanaka, Y.; Niwa, S. *Nat. Rev. Mol. Cell Biol.* 2009, 10, 682-696.

[60] Bernstein, J. G.; Boyden, E. S. *Trends Cogn. Sci. (Regul. Ed.)* 2011, 15, 592-600.

[61] Bernard, C.; Anderson, A.; Becker, A.; Poolos, N. P.; Beck, H.; Johnston, D. *Science* 2004, 305, 532-535.

[62] Kole, M. H.; Ilschner, S. U.; Kampa, B. M.; Williams, S. R.; Ruben, P. C.; Stuart, G. J. *Nat. Neurosci.* 2008, 11, 178-186.

[63] Dorval, A. D.; White, J. A. *J. Neurosci.* 2005, 25, 10025-10028.

[64] White, J. A.; Klink, R.; Alonso, A.; Kay, A. R. *J. Neurophysiol.* 1998, 80, 262-269.

[65] Schneidman, E.; Freedman, B.; Segev, I. *Neural Comput* 1998, 10, 1679-1703.

[66] Tadross, M. R.; Tsien, R. W.; Yue, D. T. *Proc. Natl. Acad. Sci. U.S.A.* 2, 013, 110, 15794-15799.

[67] Shuai, J. W.; Jung, P. *Proc. Natl. Acad. Sci. U.S.A.* 2003, 100, 506-510.

[68] Cao, Y. Q.; Piedras-Renteria, E. S.; Smith, G. B.; Chen, G.; Harata, N. C.; Tsien, R. W. *Neuron* 2004, 43, 387-400.

[69] Ianoul, A.; Street, M.; Grant, D.; Pezacki, J.; Taylor, R. S.; Johnston, L. J. *Biophys. J.* 2004, 87, 3525-3535.

[70] Brohawn, S. G.; Su, Z.; MacKinnon, R. *Proc. Natl. Acad. Sci. U.S.A.* 2, 014, 111, 3614-3619.

[71] Sasmal, D. K.; Lu, H. P. *J. Am. Chem. Soc.* 2014, 136, 12998-13005.

[72] Borisenko, V.; Lougheed, T.; Hesse, J.; Fureder-Kitzmuller, E.; Fertig, N.; Behrends, J. C.; Woolley, G. A.; Schutz, G. J. *Biophys. J.* 2003, 84, 612-622.

[73] Gonzalez, J. E.; Oades, K.; Leychkis, Y.; Harootunian, A.; Negulescu, P. A. *Drug Discov. Today* 1999, 4, 431-439.

What is claimed is:

1. A method for obtaining partial sequence information from a target protein, comprising
   denaturing and elongating a protein,
   attaching docking strands to particular amino acids in the protein,
   capturing the protein on a substrate,
   repeatedly contacting the captured protein with fluorescently-labeled imager strands that transiently bind to the docking strand, and
   imaging the substrate, thereby locating the particular amino acids in the protein.

2. The method of claim 1, wherein the protein is modified with a click chemistry reacting group prior to or at the same time as docking strands are attached.

3. The method of claim 2, wherein the click chemistry reacting group is trans-cyclooctene (TCO).

4. The method of claim 3, wherein the substrate comprises a plurality of counter-acting click chemistry groups.

5. The method of claim 4, wherein the counter-acting click chemistry groups are 1,2,4,5-tetrazine (TZ).

6. The method of claim 1, wherein the particular amino acids are amine-containing amino acids, optionally wherein the docking strands are attached to the amine-containing through an NHS-ester or an imidoester.

7. The method of claim 1, wherein the particular amino acids are lysines, optionally wherein the docking strands are attached to the lysines through an NHS-ester or an imidoester.

8. The method of claim 1, wherein the particular amino acids are sulfhydryl-containing amino acids, optionally wherein the docking strands are attached to the sulfhydryl-containing amino acids through a maleimide group, a haloacetyl group, or a pyridyldisulfide.

9. The method of claim 1, wherein the particular amino acids are cysteines, optionally wherein the docking strands are attached to the cysteines through a maleimide group, a haloacetyl group, or a pyridyldisulfide.

10. The method of claim 1, wherein the particular amino acids are carboxyl-containing amino acids, optionally wherein the docking strands are attached to the carboxyl-containing amino acids through a carbodiimide.

11. The method of claim 1, wherein the particular amino acids are aspartic acid, optionally wherein the docking strands are attached to the aspartic acid through a carbodiimide.

12. The method of claim 1, wherein the particular amino acids are glutamic acid, optionally wherein the docking strands are attached to the glutamic acid through a carbodiimide.

13. The method of claim 1, wherein the captured target protein is denatured, stretched, and immobilized on the substrate.

14. The method of claim 13, wherein the target protein is denatured using a denaturant selected from the group consisting of SDS, detergent, organic solvents, acids and bases.

15. The method of claim 1, wherein the protein is denatured and/or elongated using an amphiphilic agent.

16. The method of claim 15, wherein the protein is denatured and/or elongated using SDS.

17. The method of claim 1, wherein the protein is captured on the substrate in an electric field.

18. The method of claim 1, wherein imager strands for a single amino acid are contacted to the protein and imaged consecutively.

19. The method of claim 1, wherein imager strands for different amino acids are contacted to the protein consecutively, optionally wherein different amino acids are imaged consecutively or simultaneously.

20. The method of claim 1, wherein the location of the particular amino acids is determined with a 5 nm resolution.

21. The method of claim 1, wherein the docking strands comprise a photo-cleavable linker, and optionally the docking strands are removed by ultraviolet irradiation once imaging based on the particular amino acid is complete.

* * * * *

UNITED STATES PATENT AND TRADEMARK OFFICE
CERTIFICATE OF CORRECTION

PATENT NO. : 10,006,917 B2
APPLICATION NO. : 14/742662
DATED : June 26, 2018
INVENTOR(S) : Mingjie Dai et al.

Page 1 of 1

It is certified that error appears in the above-identified patent and that said Letters Patent is hereby corrected as shown below:

In the Specification

Please insert the following paragraph at Column 1, Line 11, (approx.) after the "Related Applications" paragraph and before the subtitle "Background.":
--GOVERNMENT LICENSE RIGHTS
This invention was made with government support under OD007292 and EB018659 awarded by National Institutes of Health. The government has certain rights in the invention.--

Signed and Sealed this
Fifth Day of May, 2020

Andrei Iancu
*Director of the United States Patent and Trademark Office*